United States Patent
Estes et al.

(10) Patent No.: US 6,609,517 B1
(45) Date of Patent: Aug. 26, 2003

(54) METHOD AND APPARATUS FOR PROVIDING POSITIVE AIRWAY PRESSURE TO A PATIENT

(75) Inventors: Mark C. Estes, Harrison City, PA (US); Douglas M. Machlenburg, Pittsburgh, PA (US); John H. Fiore, Monroeville, PA (US)

(73) Assignee: Respironics, Inc., Murrysville, PA (US)

( * ) Notice: Subject to any disclaimer, the term of this patent is extended or adjusted under 35 U.S.C. 154(b) by 0 days.

(21) Appl. No.: 09/610,733

(22) Filed: Jul. 6, 2000

Related U.S. Application Data

(63) Continuation of application No. 09/041,195, filed on Mar. 12, 1998, now Pat. No. 6,105,575, which is a continuation-in-part of application No. 08/679,898, filed on Jun. 15, 1996, now Pat. No. 5,794,615, which is a continuation-in-part of application No. 08/253,496, filed on Jun. 3, 1994, now Pat. No. 5,535,738.

(51) Int. Cl.$^7$ ............................................. A61M 16/00
(52) U.S. Cl. ........................... 128/204.23; 128/204.21; 128/204.18
(58) Field of Search ................ 128/204.18, 204.21, 128/204.23, 204.26

(56) References Cited

U.S. PATENT DOCUMENTS

| | | | | |
|---|---|---|---|---|
| 3,961,627 A | | 6/1976 | Ernst et al. ............. | 128/204.21 |
| 5,107,830 A | | 4/1992 | Younes ................... | 128/204.21 |
| 5,134,995 A | * | 8/1992 | Gruenke et al. ......... | 128/204.23 |
| 5,148,802 A | * | 9/1992 | Sanders et al. .......... | 128/204.18 |
| 5,161,525 A | | 11/1992 | Kimm et al. ........... | 128/204.23 |
| 5,188,098 A | | 2/1993 | Hoffman et al. ........ | 128/204.23 |
| 5,239,995 A | * | 8/1993 | Estes et al. ............. | 128/204.23 |
| 5,245,995 A | | 9/1993 | Sullivan et al. ......... | 128/204.23 |
| 5,259,373 A | | 11/1993 | Gruenke et al. ........ | 128/204.23 |
| 5,313,937 A | | 5/1994 | Zdrojkowski ........... | 128/204.23 |
| 5,335,654 A | | 8/1994 | Rapoport ................ | 128/204.23 |
| 5,339,807 A | | 8/1994 | Carter | |
| 5,353,788 A | | 10/1994 | Miles ...................... | 128/204.23 |
| 5,390,666 A | | 2/1995 | Kimm et al. ............ | 128/204.23 |
| 5,535,738 A | * | 7/1996 | Estes et al. .............. | 128/204.23 |
| 5,551,418 A | | 9/1996 | Estes et al. | |
| 5,794,615 A | * | 8/1998 | Estes ....................... | 128/204.23 |
| 5,810,759 A | | 9/1998 | Merz | |

FOREIGN PATENT DOCUMENTS

| | | |
|---|---|---|
| EP | 0 283 141 A2 | 2/1988 |
| EP | 0 452 092 A1 | 5/1991 |

OTHER PUBLICATIONS

Puritan–Bennett 7200a Ventilator, Option # 20/DCI, brochures AA–991 and AA–992. Sep. 1988.

(List continued on next page.)

Primary Examiner—Aaron J. Lewis
(74) Attorney, Agent, or Firm—Michael W. Haas

(57) ABSTRACT

A system including methods and apparatus for treatment of a medical disorder such as obstructive sleep apnea or congestive heart failure. The system involves applying separate and independent gains to flow rates of pressurized gas delivered to a patient during inspiratory and expiratory phases of a respiratory cycle to deliver the pressurized gas in proportion to the respective gains during inspiration and expiration. A base pressure may be applied in addition to the gain-modified pressures and an elevated pressure profile may be employed to assist or control inspiration. The system may be fully automated responsive to feedback provided by a flow sensor that determines the estimated patient flow rate. A leak computer can be included to instantaneously calculate gas leakage from the system. The system may be utilized in connection with conventional continuous positive airway pressure (bi-level PAP) equipment to effect various beneficial treatment applications.

32 Claims, 9 Drawing Sheets

OTHER PUBLICATIONS

"Mechancial Assistance to Respiration in Emphysema, Result with a Patient–Controlled Servorespirator," by James R. Harries, M.D. and John M. Tyler, M.D., published in the American Journal of Medicine, vol. 36, pp. 68–78, Jan. 1964.

"An Apparatus for Altering the Mechanical Load of the Respiratory System," by M. Younes, D. Bilan, D. Jung and H. Kroker, published by the American Physiological Society, pp. 2491–2499.

"A Device to Provide Respiratory–Mechanical Unloading," by Chi–sang Poon and Susan A. Ward, published in Mar. 1987 i IEEE Transactions on Biomedical Engineering, vol. BME–33, No. 3, pp. 361–365.

"Servo Respirator Constructed from a Positive–Pressure Ventilator," by John E. Remmers and Henry Gautier, published in Aug. 1976 in the Journal of Applied Physiology, vol. 41, No. 2, pp. 252–255.

"Effect of Nasal Continuous Positive Airway Pressure on Sleep Apnea in Congestive Heart Failure" by Yuji Takasaki, Douglas Orr, Judith Popkin, Ruth Rutherford, Peter Liu, and T. Douglas Bradley published in Am Rev Respir Dis, vol. 140, pp. 1578–1584.

"Treatment of Congestive Heart Failure and Cheyne–Stokes Respiration During Sleep by Continuous Positive Airway Pressure" by Matthew T. Naughton, Peter P. Liu, Dean C. Benard, Roger S. Goldstein and T. Douglas Bradley, pub lished in the American Journal of Respiratory and Critical Care Medicine, vol. 151, pp. 92–97, 1995.

"Effect of Continuous Positive Airway Pressure on Central Sleep Apnea and Nocturnal $PCO_2$ in Heart Failure" by Matthew T. Naughton, Dean C. Bernard, Ruth Rutherford, and T. Douglas Bradley published in the American Journal of Respiratory and Critical Care Medice, vol. 150, pp. 1599–1604, 1994.

Cardiac Output Response to Continuous Postivie Airway Pressure in Congestive Heart Failure by T. Douglas Bradley, Richard M. Holloway, Peter R. McLaughlin, Bette L. Ross, Janice Walters, and Peter P. Liu published in Am Rev Respir Dis, vol. 145, pp. 377–382, 1992.

"Evidence Keeps Mounting on Link Between Apnea and Heart Disease" by Sandra Blakeslee published in The New York Times Health, Dec. 20, 1995.

"Occult Sleep–Disordered Breathing in Stable Congestive Heart Failure" by Shahrookh Jaraheri, M.D.; Thomas J. Parker, M.D.; Laura Wexler, M.D.; Scott E. Michaels, Ph.D.; Elizabeth Stanberry, Ph.D.; Hiroshi Nishyama, M.D.; and Gary A Roselle, M.D. published originally in Annals of Internal Medicine, vol. 122; No. 7, Apr. 1, 1995.

* cited by examiner

METHOD AND APPARATUS FOR PROVIDING POSITIVE AIRWAY PRESSURE TO A PATIENT

CROSS REFERENCE TO RELATED APPLICATIONS

This is a Continuation of U.S. patent application Ser. No. 09/041,195, filed Mar. 12, 1998, now U.S. Pat. No. 6,105,575, which is a Continuation-in-Part of U.S. patent application Ser. No. 08/679,898 filed Jun. 15, 1996, now U.S. Pat. No. 5,794,615, which is a Continuation-in-Part of U.S. patent application Ser. No. 08/253,496 filed Jun. 3, 1994, now U.S. Pat. No. 5,535,738.

BACKGROUND OF THE INVENTION

1. Field of the Invention

The present invention relates generally to methods and apparatus for treating breathing and/or cardiac disorders and, more particularly, to methods and apparatus for providing a pressure to an airway of a patient during at least a portion of the breathing cycle to treat obstructive sleep apnea syndrome, chronic obstructive pulmonary disease, congestive heart failure, and other respiratory and/or breathing disorders.

2. Description of the Related Art

During obstructive sleep apnea syndrome (OSAS), the airway is prone to narrowing and/or collapse while the patient sleeps. Continuous positive airway pressure (CPAP) therapy seeks to avoid this narrowing by supplying pressure to splint the airway open. With CPAP, this splinting pressure is constant and is optimized during a sleep study to be sufficient in magnitude to prevent narrowing of the airway. Providing a constant splinting pressure, i.e., CPAP, is a simple solution to the problem posed by the collapsing airway. However, this approach exposes the patient to pressures that are higher than the pressures needed to support the airway for most of the breathing cycle.

During inspiration, the pressure created within the lungs is lower than the pressure at the nose. This pressure difference drives the flow of air into the lungs. This pressure difference creates a pressure gradient in the airway connecting the lungs with the nose. That is to say, the nose is typically at ambient pressure while the lungs and airway of the patient are at sub-ambient or negative pressures. This negative pressure acts upon the airway and contributes to its collapse. CPAP levels are typically set to raise the pressure level in the entire respiratory system to the level required to both eliminate the sub-ambient pressures generated by inspiration and overcome any mechanical collapsing forces that result from the structure of the airway tissues, muscle tone, and body position. The inspiratory pressures, i.e., inspiratory positive airway pressure or "IPAP," in bi-level positive airway pressure systems are set in a similar manner.

During exhalation, a positive pressure gradient exists between the interior of the lungs and the exterior of the body. This positive pressure gradient helps to support the airway during exhalation. At the end of exhalation, the pressure gradient is essentially zero; flow is likewise zero and the airway is unaffected by respiratory efforts. Any collapse of the airway at the end of exhalation is purely a function of the structure of the airway tissues, muscle tone, and body position. Bi-level devices seek to supply the expiratory pressure required to support the airway at the end of exhalation.

It should be noted that over the course of a breathing cycle, the pressure gradients between the lungs and the exterior of the body are not constant. The inspiratory pressure gradient falls from zero at the start of inspiration to a peak negative value and then rises back to zero at the end of inspiration. The expiratory pressure gradient rises from zero at the start of exhalation to a peak value and then falls back to zero as exhalation ends. Because the pressure gradient varies over the breathing cycle, the pressure necessary to overcome airway collapse should ideally vary over the breathing cycle.

Traditional CPAP therapy ignores these variations in pressure requirements and provides therapy at one pressure level. Conventional CPAP is rather crude and offers far from optimal therapy since the CPAP pressure is based solely on a worst-case treatment parameter, i.e., the peak pressure requirements during inspiration.

Representing an advancement over conventional CPAP, bi-level positive airway pressure (bi-level PAP) therapies seek to take advantage of the different pressure requirements to lower the pressure during exhalation. Nevertheless, bi-level therapies also fail to afford optimal treatment because the inspiratory positive airway pressure (IPAP) of bi-level PAP is again based on the patient's peak needs encountered during inspiration and remains constant over the entire inspiratory phase respiration. Also, during bi-level treatment, the expiratory position airway pressure (EPAP) remains constant and is related solely to the support needs at the end of exhalation.

In addition to OSAS, positive airway pressure therapy, such as bi-level PAP therapy, has been applied in the treatment of other breathing disorders, such as chronic obstructive pulmonary disorder (COPD). One of the problems with this mode of treatment, however, is that the patient has difficulty stopping inspiratory flow. This phenomenon arises due to the disparity between applied IPAP and the pressure needed to overcome the patient's respiratory resistance at the end of inspiration. As the former pressure typically exceeds the latter, the "surplus" IPAP at the end of inspiration leads to uncomfortable and potentially harmful hyperinflation of the patient lungs.

Conversely, in order to begin inspiratory flow, a COPD patient must reduce the pressure inside his lungs to a pressure that is less than the ambient pressure at the inlet of his respiratory system. Due to the condition commonly known as "Auto-PEEP," the pressure in the patient's lungs is typically above ambient pressure at the end of exhalation. The patient's breathing muscles thus must perform additional work to expand the lungs and thereby reduce lung pressure below ambient before flow into the lungs can occur. Auto-PEEP is typically treated with a form of resistive counter pressure known as PEEP (positive end expiratory pressure). PEEP is set at a level just below the patient's Auto-PEEP level, thereby reducing the amount of breathing work required to initiate inspiratory flow.

With conventional treatments, such as pressure support, CPAP or bi-level therapy, PEEP is achieved by applying the same pressure over the entire phase of expiration, e.g., the EPAP phase of bi-level PAP therapy. It should be noted that EPAP is not synonymous with PEEP. EPAP indicates a constant pressure delivered to the patient throughout exhalation, while PEEP indicates positive end expiratory pressure. By definition, the PEEP pressure is only required at the end of exhalation. As such, the administration of EPAP throughout the expiratory cycle to assure that satisfactory PEEP is maintained undesirably contributes to the breathing work that a patient must perform during exhalation.

In addition to CPAP and bi-level PAP, other systems have been proposed for clinical research and/or therapeutic application, including treatment of OSAS, COPD and other breathing disorders, that offer an assortment of methods and apparatus by means of which a subject's respiratory efforts may be induced, superseded, assisted and/or resisted. Some of these systems perform their prescribed functions responsive to one or more parameters associated with a subject's respiratory activity including, but not limited to, inspiratory and/or expiratory flow, inspiratory and/or expiratory pressure, tidal volume and symptoms indicative of airway obstruction, e.g., snoring sounds. Some achieve their objectives transthoracically while others deliver air at positive or negative pressure directly to the subject's airway.

An early example of such a system, commonly referred to as an "iron lung," is disclosed in a publication entitled "Mechanical Assistance to Respiration in Emphysema, Results with a Patient-Controlled Servorespirator," authored by James R. Harries, M.D. and John M. Tyler, M.D., published in the American Journal of Medicine, Vol. 36, pp. 68–78, January 1964. The iron lung proposed in that publication is a respirator designed to apply and remove transthoracic pressure to and from the exterior surface of the body of a subject who sits in a large pressurizable chamber in order to assist the patient's respiratory efforts (i.e., the iron lung applies negative pressure during inspiration and either ambient or positive pressure during expiration). Sophisticated for its day, the apparatus continually controlled the internal chamber pressure in response to the patient's spontaneous respiration, specifically in response to detected respiratory flow or volume. Indeed, a signal obtained from a strain gauge pneumograph fastened around the patient's chest was electrically separated into three components: one proportional to volume, another to inspiratory flow and a third to expiratory flow. Each component was assigned a separate gain control. The component signals are then recombined to control the pressure in the chamber by means of an electrically driven variable valve situated between a blower and the chamber.

Although effective for their intended purposes, this and other iron lung devices have generally fallen into disfavor because of their bulk, inconvenience, cost and limited application. That is to say, because of their size and cost such equipment is purchased and maintained essentially exclusively by medical facilities such as hospitals and clinics. Further, iron lungs do not lend themselves to treatment of OSAS and related disorders where comfort and unobtrusiveness are critical for patient compliance and treatment efficacy. This is because negative pressure applied during inspiration compounds the factors that operate to collapse the airway during an inspiratory phase.

An essay entitled, "An Apparatus for Altering the Mechanical Load of the Respiratory System," authored by M. Younes, D. Bilan, D. Jung and H. Krokes, and published in 1987 by the American Physiological Society, pp. 2491–2499, discloses a system for loading and unloading of a subject's respiratory efforts to effect various respiratory responses. The system may load or unload during inspiration, expiration, or both, to assist or resist a subject's spontaneous respiratory activity. The system may apply a continuous positive or negative pressure directly to the subject's airway and loading or unloading occurs via a command signal generated by detected respiratory flow, volume, applied voltage, an external function, or other source.

A drawback to this system, however, is that a single resistive gain is chosen for resistive loading or unloading. This single gain is applied to a "half-wave" of the respiratory cycle (either inspiration or expiration) or the "full-wave" thereof (both inspiration and expiration). In other words, under full-wave respiratory loading or unloading, a single chosen gain value is employed during both inspiration and expiration. Thus, a gain that may produce favorable results in regard to reducing breathing work during inspiration, for example, may cause less than desirable or even detrimental consequences during expiration. The converse is true for a gain selected specifically for optimizing expiratory work reduction.

In addition, the Younes et al. system operates as a closed, leak-proof system. Hence, to predict its ability to function in an open, leak-tolerant system would be problematic. As such, whether it may be adapted to OSAS treatment, which invariably involves some degree of known and unavoidable unknown system leakage, is suspect.

U.S. Pat. No. 5,107,830 to Younes essentially reiterates all of the "breathing assist" (unloading) disclosure that is covered in the Younes, et al. American Physiological Society publication discussed above. In the system disclosed in U.S. Pat. No. 5,107,830, however, the adjustable pressure gain is only realized during inspiration because pressure output is set to zero during exhalation. Additionally, output pressure is calculated as a function of both detected patient inspiratory flow and volume. Furthermore, the system is applicable to COPD but not OSAS therapy.

An article entitled "A Device to Provide Respiratory-Mechanical Unloading," authored by Chi-sang Poon and Susan A. Ward and published in March 1987 in IEEE Transactions on Biomedical Engineering, Vol. BME-33, No. 3, pp.361–365, is directed to an apparatus which functions somewhat similar to one mode of operation described in both Younes disclosures. That is, the Poon, et al. device may operate to unload a subject's breathing, but only during inspiration. Poon, et al. provide their inspiratory assistance by establishing a positive mouth pressure throughout inspiration in a constant proportion to instantaneous flow. The constant proportion is achieved by (1) selecting a desired gain for a detected positive mouth pressure signal, (2) calculating the ratio of the gain-modified mouth pressure signal over a detected signal reflecting instantaneous flow, (3) comparing the calculated ratio to a selected reference ratio to generate a valve motor control signal, and (4) using the valve motor control signal to operate a motor that drives a servo valve to control the positive pressure applied to the subject's airway. Thus, the apparatus output pressure is determined as a function of both detected pressure and flow. Further, the pressure must be output at a value sufficient to maintain a constant ratio of pressure to flow.

A publication entitled "Servo Respirator Constructed from a Positive-Pressure Ventilator," by John E. Remmers and Henry Gautier, which was published in August, 1976 in the Journal of Applied Physiology, Vol. 41, No. 2, pp. 252–255, describes a modified ventilator that may function as a "demand" respirator generating a transthoracic pressure proportional to phrenic efferent respiratory discharge. Phrenic efferent respiratory discharge is an indication of the outgoing brain signal to the phrenic nerve, which controls diaphragm function. A phrenic efferent respiratory discharge signal causes the diaphragm to contract whereby the subject exerts an inspiratory effort. The phrenic efferent respiratory discharge serves as the apparatus command signal and is processed to produce a moving time average (MTA) and the subject's tracheal pressure serves as a negative feedback signal. Like the Poon et al. device, the Remmers et al. apparatus provides respiratory assistance only during inspiration.

An apparatus for automatically regulating the flow and pressure output of a respirator is disclosed in U.S. Pat. No.

3,961,627 to Ernst et al. Like the aforementioned Poon et al. device, however, the Ernst et al. apparatus relies upon an unduly complicated scheme dependent upon detected respiratory pressure and flow in calculating delivered output flow and pressure. More particularly, Ernst et al. propose regulating the delivered flow and pressure of a respiration gas in a respirator during the respiration cycle in which the actual flow and pressure of the respiration gas am measured via a measuring device arranged proximate a patient interface. The measured values are converted into electrical signals and the flow and pressure of the respiration gas are controlled during the inspiration and expiration portions of the respiration cycle via a valve arranged between a respiration gas source and the measuring device. The method for regulating the flow and pressure output comprises (1) measuring the actual flow of respiration gas proximate the patient, (2) measuring the actual pressure of respiration gas proximate the patient, (3) calculating nominal values of flow and pressure from preselected fixed values and the actual values, (4) comparing the actual values measured for the flow and pressure with the nominal values, and (5) obtaining from the comparison a control signal for modulating the valve and thereby regulating the flow and pressure of the respiration gas.

Additionally, apart from its utilization of two detected respiratory parameters (flow and pressure) and the complex manner in which these and other variables are reiteratively processed to produce apparatus flow and pressure output, the Ernst et al. system, although capable of delivering a base pressure equivalent to a patient's required end expiratory pressure, is nevertheless unable to deliver any pressure less than the base pressure. Consequently, the Ernst et al. apparatus requires the patient to perform more breathing work than is necessary to satisfy his respiratory needs, especially in the expiratory phase of a respiration cycle, thereby deleteriously affecting the patient's comfort and likelihood of continued compliance with the treatment.

In addition to the treatment of breathing disorders, positive airway pressure therapy has been applied to the treatment of congestive heart failure (CHF). In using CPAP on CHF, the effect of the CPAP is to raise the pressure in the chest cavity surrounding the heart. This has the impact of reducing the amount of pressure the heart has to pump against to move blood into the body. By reducing the pressure the heart works against, the work required of the heart is reduced. This allows the sick heart to rest and potentially to get better.

The pressure in the chest cavity is also impacted by respiration effort. With inspiration, the pressure in the chest is reduced (negative relative to resting pressure) due to inspiratory effort. This forces the heart to pump harder to move blood into the body. With expiration, the pressure in the chest is slightly increased (positive relative to resting pressure) due to the elastic properties of the chest. This allows the heart to decrease its efforts to pump blood. While conventional CPAP can help the heart rest, it has negative aspects for the patient such as increased work of exhalation and discomfort from the pressure.

SUMMARY OF THE INVENTION

It is an object of the present invention to provide an uncomplicated system operable to deliver pressurized air to the airway of a patient and readily adaptable to the treatment of OSAS, COPD and other respiratory and/or pulmonary disorders that does not suffer from the disadvantages of conventional pressure application techniques. This object is achieved by providing an apparatus for delivering pressurized breathing gas to an airway of a patient. The apparatus, which is referred to below as a "proportional positive airway pressure" or "PPAP" apparatus, includes a gas flow generator, a patient interface that couples the gas flow generator to the patient's airway, a sensor that detects a fluid characteristic associated with a flow of gas within the patient interface, a pressure controller that regulates the pressure of breathing gas provided to the patient, and a control unit that controls the pressure controller.

The control unit controls the pressure controller so that the breathing gas is delivered to the patient at a minimally sufficient pressure during at least a portion of a breathing cycle to perform at least one of the following functions at any given moment: (1) reduce cardiac preload and afterload, in which case the minimally sufficient pressure is a summation of a pressure needed to reduce cardiac preload and afterload in an absence of respiratory loading and a pressure needed to overcome an impact of respiratory loading on cardiac preload and afterload, and (2) prevent airway collapse, in which case the minimally sufficient pressure is a summation of a pressure needed to prevent airway collapse due to mechanical forces resulting from the structures of the patient and a pressure needed to overcome airway collapse due to respiratory effort. The apparatus also includes a selector unit that establishes a first gain. The control unit controls the pressure controller so as to deliver the breathing gas at the minimally sufficient pressure during at least a portion of the breathing cycle based on the first gain and the signal from the sensor.

The PPAP system of the present invention provides airway pressure that is lower than pressures typically necessary to treat OSAS, which is normally treated using conventional CPAP or bi-level PAP therapy. With PPAP, the patient receives exhalation pressures lower than conventional bi-level PAP expiratory positive airway pressure levels and well below conventional CPAP levels. Also, the average pressure delivered during inspiration can be lower than conventional or bi-level PAP inspiratory positive airway pressure or CPAP levels, whereas peak PPAP pressure is roughly equivalent to conventional IPAP or CPAP levels. The PPAP pressure range (peak inspiratory pressure to minimum expiratory pressure) is generally between 2 to 20 cm $H_2O$, with typical values in the 8 to 14 cm $H_2O$ range. This is consistent with bi-level PAP therapy where significant comfort/compliance is found with peak inspiratory to minimum expiratory pressure differentials of 6 cm $H_2O$ or more. The complexity of titration using the apparatus of the instant invention is roughly equivalent to current bi-level PAP titration. In addition, the titration system may incorporate a feedback circuit to provide fully automated PPAP.

Similar to treatment of OSAS, PPAP also delivers mean airway pressure that is lower than pressures typically necessary to treat COPD using conventional bi-level PAP therapy with PEEP or proportional assist ventilation (PAV) with PEEP. That is, with PPAP, the patient receives average exhalation pressures lower than conventional EPAP levels, average inspiration pressures lower than conventional IPAP, and peak PPAP pressure roughly equivalent to conventional IPAP pressures and conventional peak PAV levels. Hence, less breathing work is required with PPAP than with conventional PAV or bi-level treatments of COPD or OSAS.

It is a further object of the present invention to provide a modified CPAP apparatus that is capable of easily detecting exhalation and modifying the exhalation pressure to match a selected pressure profile. This object is achieved by providing an apparatus that includes a gas flow generator, a patient interface that couples the gas flow generator to the patient's airway, a sensor that detects a physiological condition that is suitable for use to differentiate between an expiratory phase and an inspiratory phase of a breathing cycle, a pressure controller that regulates the pressure of breathing gas provided to the patient, and a control unit that controls the pressure controller. More specifically, the control unit causes the breathing gas to be delivered at a first pressure level during an inspiratory phase of the breathing cycle, which is consistent with the operation of a conventional CPAP device. However, the control unit causes the breathing gas to be delivered in accordance with a predetermined pressure profile during the expiratory phase of the breathing cycle. This profile provides a decrease in the EPAP provided to the patient. Because the pressure profile can be obtained by controlling the operation of existing CPAP devices, it can be readily implemented on many such devices; thereby providing a better therapy for a patient using existing devices.

It is yet another object of the present invention to provide a system for eliminating oscillations in the flow provided during patient exhalation that can occur with use of the PPAP device. According to a first embodiment of the present invention, this object is achieved by causing the pressure controller to provide a pressure to the patient during expiration that is the greater of (1) a first minimally sufficient pressure that is determined by applying a gain to the signal output by the sensor and (2) a second minimally sufficient pressure that corresponds to a current pressure being provided to the patient. By ensuring that the pressure provided to the patient is always the greater of these two pressures, the pressure received by the patient during expiration does not oscillate, because should the pressure to be provided to the patient begin to decrease below the current pressure, the device will not use the calculated pressure, but will continue to provide the patient with the current pressure, thereby preventing a pressure decrease below the current pressure.

According to a second embodiment of the present invention, the object of preventing oscillations in the patient flow provided during expiration is achieved by causing the pressure controller to provide an expiration pressure that is determined based on a volume of gas to be exhaled and a gain. This gain can be the same gain or a different gain from that applied to the signal from the sensor during inspiration (if any). The volume of gas to be exhaled corresponds to a difference between the current volume of gas in the patient and the volume of gas in the patient at rest.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE PRESENTLY PREFERRED EMBODIMENTS

Figure 1:
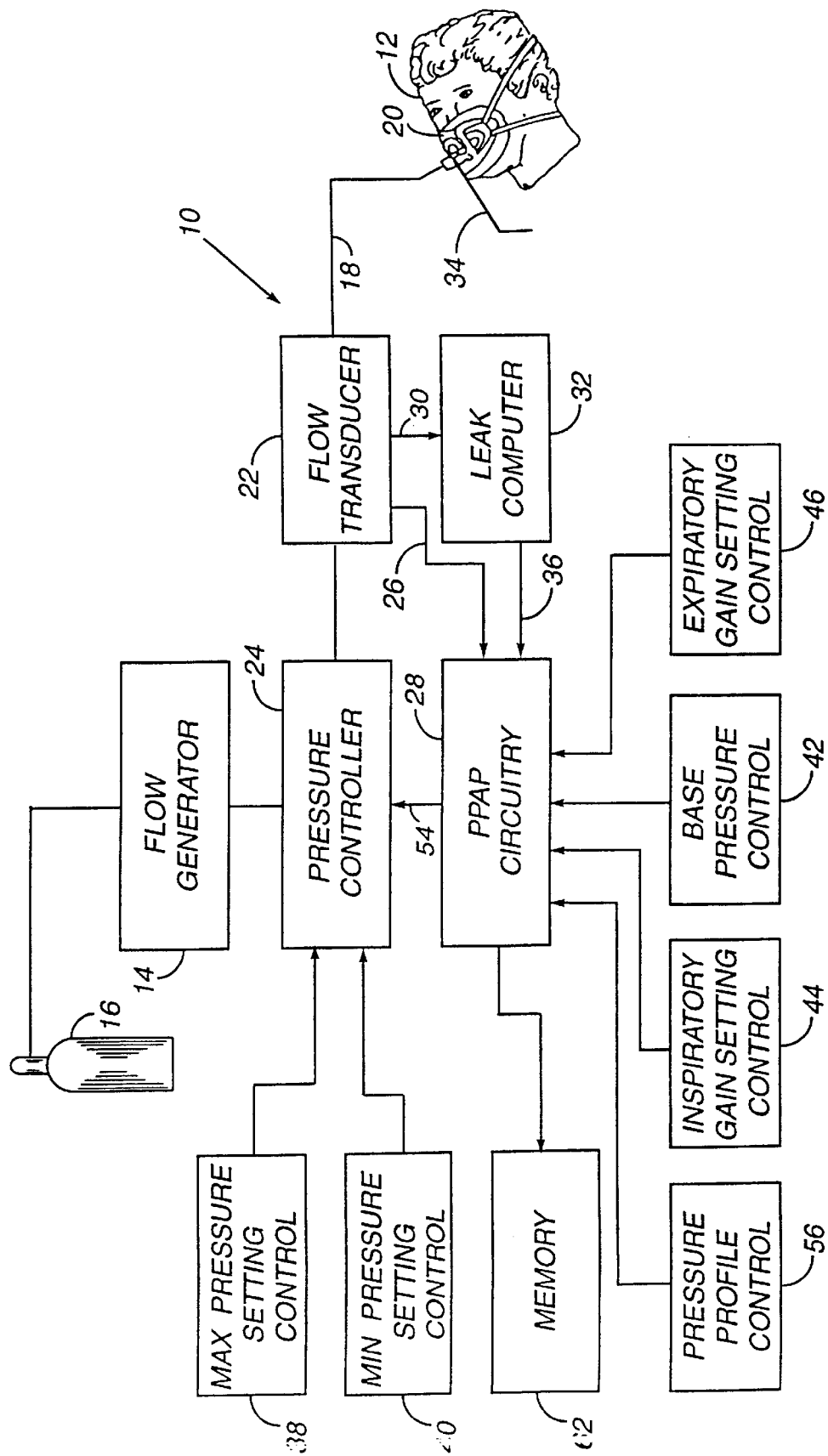
FIG. 1 is a functional block diagram of an apparatus according to the instant invention.

There is generally indicated at 10 in FIG. 1 a proportional positive airway pressure apparatus according to a presently preferred embodiment of the instant invention and shown in the form of a functional block diagram. Apparatus 10 is operable according to a novel process to deliver breathing gas, such as air, oxygen or a mixture thereof, at relatively higher and lower pressures (i.e., generally equal to or above ambient atmospheric pressure) to a patient 12 in proportion to the patient's respiratory flow for treatment of OSAS, COPD and other respiratory disorders.

Apparatus 10 includes a gas flow generator 14, such as a conventional CPAP or bi-level PAP blower, i.e., a centrifugal blower with a relatively steep pressure-flow relationship at any constant speed, that receives breathing gas from any suitable source, e.g., a pressurized bottle 16 of oxygen or air, the ambient atmosphere, or a combination thereof. The gas flow from flow generator 14 is passed via a delivery conduit 18 to a breathing appliance or patient interface 20 of any suitable known construction that is worn by patient 12. In an exemplary embodiment of the present invention, the conduit 18 is a large bore flexible tube and the patient interface 20 is either a nasal mask or a full face mask, as shown. Other breathing appliances that may be used in lieu of a mask include a mouthpiece, a nasal seal, nasal prongs or cannulae, an endotracheal tube, a trachea adapter or any other suitable appliance for interfacing between a source of breathing gas and a patient. Also, the phrase "patient interface" can encompass more that the interface worn by the patient. For example, the patient interface can include delivery conduit 18 and any other structures that connect the source of pressurized breathing gas to the patient.

The apparatus also includes a sensor, such as a flow transducer 22 or similar flow sensing element, situated within or near the breathing circuit, i.e., the patient interface 20, conduit 18 or gas flow generator 14. Flow transducer 22 may be any suitable gas flow meter, such as, for example, a bidirectional dynamic mass flow sensor. Preferably, however, the flow transducer is a pressure responsive sensor for detecting the magnitude of the pressure gradients between the inlet of the patient's airway and his lungs. Within the scope of the present invention, flow and respiratory pressure gradient are highly correlated.

In accordance with a presently preferred embodiment, the flow transducer 22 is interposed in line with conduit means 18, most preferably downstream of a pressure controller 24. The flow transducer generates output signals that are provided, as indicated by reference numeral 26, to PPAP circuitry 28 described in greater detail hereinafter. The output signals include first flow rate signals indicative of inspiration by the patient and second flow rate signals indicative of the patient's expiration. The signals are continuously transmitted and correspond to the instantaneous flow rate of breathing gas within conduit means 18.

In addition, the output from flow transducer 22 is also desirably provided, as indicated by reference numeral 30, to an optional leak detecting system 32. A suitable leak detector for present purposes is that disclosed in U.S. Pat. No. 5,148,802, the disclosure of which is incorporated herein by reference. However, other techniques for substantially instantaneously calculating system leakage, including both known leakage, such as that discharged through a mask exhaust port 34, and unknown leakage, such as that at various conduit couplings or at the patient contact site of the patient interface 20, are acceptable. With any non-invasive embodiment of the present invention, i.e., not involving an endotracheal tube or trachea adapter, the patient flow must be estimated taking into account the aforesaid known and unknown system leaks.

The output signal from the leak detecting system 32 is provided, as at 36, to PPAP circuitry 28. In this way, the PPAP circuitry logic continuously compares the output from flow transducer 22 with that from leak detecting system 32 to discriminate that portion of system flow associated with the patient's respiration from that caused by system leakage. As a result, PPAP circuitry 28 more precisely controls the output of the pressure controller 24 as a function of patient respiratory flow, rather than overall system flow.

If formed as a mask, as illustrated, patient interface 20 commonly includes, as mentioned above, a suitable exhaust system, schematically indicated at 34, to exhaust breathing gases during expiration. Exhaust system 34 preferably is a continuously open port that imposes a suitable flow resistance upon exhaust gas flow to permit pressure controller 24, located in line with conduit 18 between flow generator 14 and patient interface 20, to control the pressure of air flow within the conduit and thus within the airway of the patient. For example, exhaust port 34 may be of sufficient cross-sectional flow area to sustain a continuous exhaust flow of approximately 15 liters per minute at a system pressure of 10 cm $H_2O$. The flow via exhaust port 34 is one component, and, typically, the major component of the overall system leakage, which is an important parameter of system operation. In an alternative embodiment, it has been found that a non-rebreathing valve may be substituted for the continuously open port.

Pressure controller 24 controls the pressure of breathing gas within conduit 18 and thus within the airway of the patient. Pressure controller 24 is located preferably, although not necessarily, downstream of flow generator 14 and may take the form of an adjustable, electronically-controlled valve.

Apparatus 10 also desirably includes a safety circuit, preferably comprising an adjustable maximum pressure setting control 38 and an adjustable minimum pressure setting control 40 operatively connected to pressure controller 24. The safety circuit allows the manufacturer, the patient or his overseeing health care professional to selectively establish minimum and maximum system output pressures below and above which the system will not dispense pressurized gas. The minimum pressure will, of course, be at least zero and, preferably, a threshold pressure sufficient to maintain pharyngeal patency during expiration. The maximum pressure, on the other hand, will be a pressure somewhat less than that which would result in over-inflation and perhaps rupture of the patient's lungs. The safety circuit functions differently than the pressure controls which determine, for instance, the CPAP prescription pressure or the IPAP and EPAP prescription pressures used in bi-level PAP therapy. That is, instead of establishing lower and upper prescription pressures to be administered during normal usage of the apparatus (subject to the influence of the PPAP circuitry 28), the maximum and minimum pressure setting controls 38 and 40 set absolute minimum and maximum fail-safe output pressure limits which are not to be exceeded. Thus, the danger of potential physical harm to the patient in the even of malfunction of other system components, e.g., the prescription pressure controls, is effectively eliminated.

PPAP circuitry 28, according to the present invention, is subject to the influence of additional essential controls, including a base pressure control 42, an inspiratory gain setting control 44, and an expiratory gain setting control 46. The base pressure control 42 establishes a base pressure (Pbase), usually greater than or equal to zero and conceptually equal to the EPAP level in bi-level therapy, sufficient to maintain airway patency at the beginning and end of exhalation. The inspiratory gain setting control 44 permits selection of a resistive gain ($Gain_{Insp}$) to be applied to the detected inspiratory flow. Similarly, the expiratory gain setting control 46 enables selection of a resistive gain ($Gain_{Insp}$) to be applied to the detected expiratory flow.

In a broad sense, PPAP therapy and the PPAP apparatus 10 constitute a novel system providing pressure to a patient via nasal, nasal/oral, oral, or trachea interface to treat OSAS, COPD and other breathing disorders. The pressure delivered to the patient is a function of the patient flow rate. The function can be described as follows:

$$P\text{delivered} = P\text{base} + \text{Gain} * \text{Flow}$$

where:

"Pdelivered" is the pressure delivered to the patient interface;

"Pbase" is the base line pressure (greater than or equal to zero and conceptually equal to EPAP);

"Flow" is the estimated patient flow rate determined by the flow transducer; and "Gain" is the constant used to augment pressure based on the flow rate. The gain constant can further be refined to allow one constant for inspiration (positive flow) and a different constant for exhalation (negative flow).

Figure 3A:
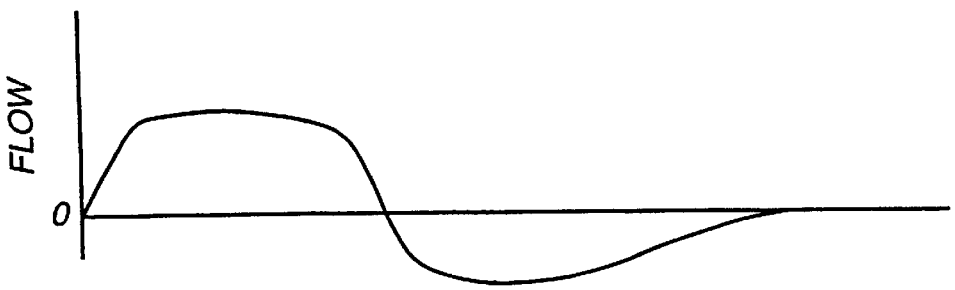
FIGS. 3A and 3B are flow and pressure diagrams, respectively, graphically representing the general manner in which an apparatus according to the instant invention outputs pressurized breathing gas in a proportional relation to the patient flow in both the inspiratory and expiratory phases of a single respiratory cycle.
Figure 3B:
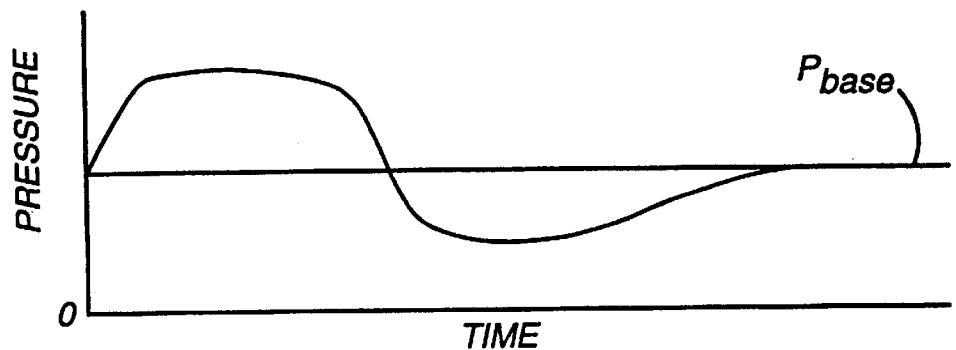

FIGS. 3A and 3B represent flow and pressure diagrams, respectively, graphically depicting the manner in which apparatus 10 outputs pressurized breathing gas in proportional relation to patient flow, as detected by flow transducer 22, in both the inspiratory and expiratory phases of a respiratory cycle. The pressure curve of FIG. 3B reflects a situation where the same gain is chosen for both inspiratory and expiratory flow. Conceivably, essentially the same pressure curve may be generated by the apparatus disclosed in the aforementioned essay entitled "An Apparatus for Altering the Mechanical Load of the Respiratory System," by Younes, et al. which may use a single resistive gain applicable to both inspiration and expiration.

With PPAP apparatus 10, however, separate and independent gains may be chosen for inspiration and expiration, whereby gains best suited for optimizing performance, i.e., minimizing breathing work, may be precisely matched with each of the inspiratory and expiratory phases. Thus, the function of the apparatus described in the Younes et al. article corresponds to a special and relatively limited application of the present invention where the selected inspiratory and expiratory gains are identical.

As is far more often the case, however, an optimum inspiratory gain is not the optimum expiratory gain and vice versa. Thus, the pressure output of the PPAP apparatus 10 is more accurately described according to the following functions, which functions can be encoded into the PPAP circuitry 28.

$$P\text{inhalation} = P\text{base} + \text{Gain} * \text{Flow}$$

and $$P\text{exhalation} = P\text{base} + \text{Gain}_{Exp} * \text{Flow}$$

Where:

"$\text{Gain}_{Insp}$" is the constant used during inspiration (positive flow) to boost pressure based on the flow rate; and "$\text{Gain}_{Exp}$" is the constant used during exhalation (negative flow) to reduce pressure based on the flow rate.

The gain typically selected has a range of about 0 to 10 cm $H_2O$/liter/second for inspiration. The gain chosen for exhalation is normally lower than the inspiratory gain, e.g., values in the range of 0 to 4 cm $H_2O$/liter/second, although higher gain values may be chosen for inspiration and/or expiration, if such is desired or necessary.

Regardless of the chosen gain values, applying a flow signal derived from a normal respiratory pattern will result in a pressure rise above Pbase during inspiration and will drop below Pbase during exhalation. When patient flow is near zero, i.e., at the beginning and end of inspiration, as well as the beginning and end of exhalation, the output pressure approaches Pbase.

Figure 4A:
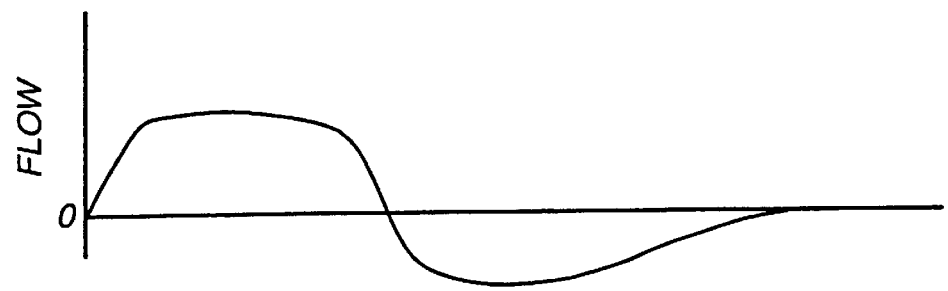
FIGS. 4A and 4B are flow and pressure diagrams, respectively, similar to FIGS. 3A and 3B, exemplifying a number of apparatus output pressure curves that are achieved through selective adjustment of inspiratory and expiratory gain setting controls of the proportional positive airway pressure circuitry of the instant invention.
Figure 4B:
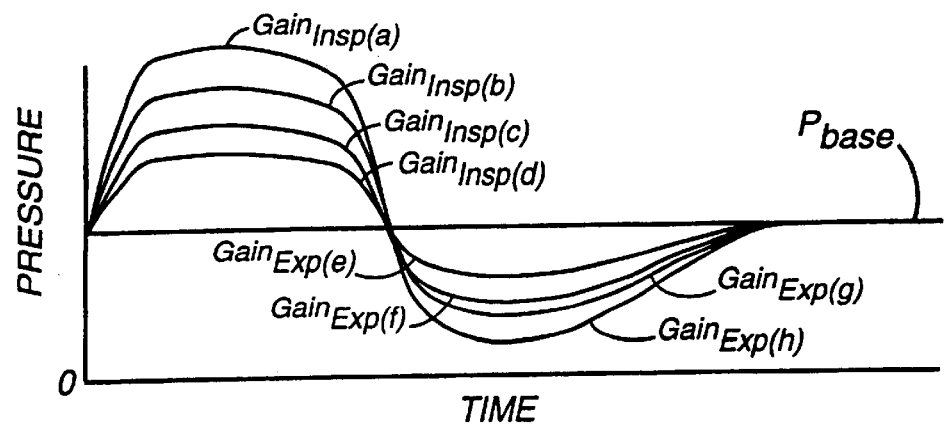

FIGS. 4A and 4B perhaps most clearly exemplify the effect that the selection of different gains for both the inspiratory and expiratory phases of a respiratory cycle has upon the pressure output curve. $\text{Gain}_{Insp(a)}$, $\text{Gain}_{Insp(b)}$, $\text{Gain}_{Insp(c)}$ and $\text{Gain}_{Insp(d)}$ represent, in descending order, several of an infinite range of gain values that may be applied during inspiration. Similarly, $\text{Gain}_{Exp(e)}$, $\text{Gain}_{Exp(f)}$, $\text{Gain}_{Exp(g)}$ and $\text{Gain}_{Exp(h)}$ indicate increasing expiratory gain values. With different gain settings, any number of wave forms can be generated. For example, a high setting may be established for $\text{Gain}_{Insp}$ and a low setting for $\text{Gain}_{Exp}$, or vice versa, or the gain settings for inspiratory flow and expiratory flow may be the same.

In one embodiment of the present invention, PPAP therapy seeks to provide only the pressure that is necessary to prevent airway collapse at any given moment during the breathing cycle. This will generally result in supplying, at appropriate times, maximum pressure only when peak negative airway inspiratory pressures are detected and minimum pressure only when peak positive airway exhalation pressures are detected. At all other times during the breathing cycle, the PPAP apparatus delivers air at a variable pressure responsive to the patient's respiratory efforts in a range between the maximum and minimum pressures. As mentioned above, PPAP therapy also involves the administration of a base pressure of zero or greater to which the product of a selected gain times instantaneous flow (inspiratory and expiratory) is continuously added to produce the instantaneous output pressure of the PPAP apparatus. An identical gain may be selected for inspiration and expiration, or different gain values may be independently selected for inspiration and expiration. The base pressure will be the pressure necessary to overcome any mechanical collapsing forces that result from the structure of the airway tissues, muscle tone, and body position. In other words, the base pressure is generally equivalent to the expiratory positive airway pressure or "EPAP" typically used in bi-level PPAP therapy.

Figure 5A:
FIGS. 5A and 5B are flow and pressure diagrams, respectively, similar to FIGS. 3A and 3B, contrasting a pressure output curve typical of an apparatus according to the instant invention with pressure output curves of a conventional respiratory assistance apparatus.
Figure 5B:
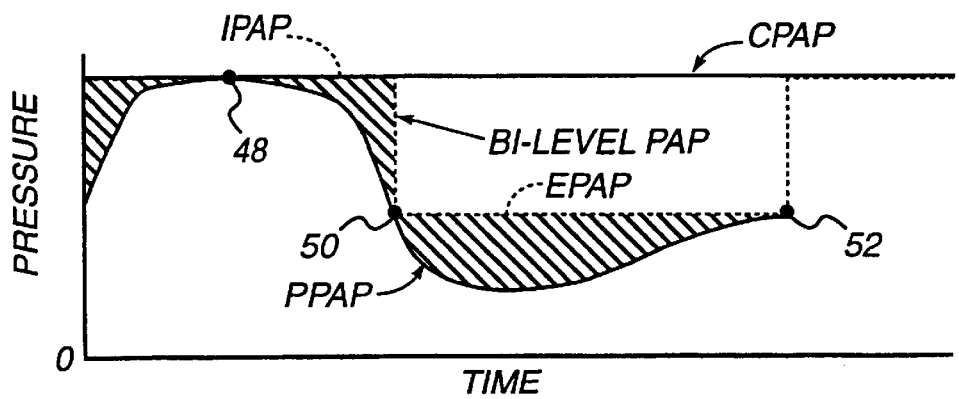

In this connection, FIG. 5B illustrates the pressure output curve generated by the PPAP apparatus 10 vis-a-vis conventional CPAP and bi-level PAP apparatus over a single respiratory cycle. So long as the appropriate inspiratory and expiratory splint pressures are applied at point 48 (peak inspiratory flow), point 50 (beginning of exhalation) and point 52 (end of exhalation), less pressure may be provided at all other times during the breathing cycle than is normally supplied by conventional CPAP or bi-level PAP therapy. This reduced output pressure is represented by the "PPAP" curve of FIG. 5B. The hatched areas of that figure reflect the difference in pressures provided by PPAP and the EPAP and EPAP phases of bi-level PAP during a typical respiratory cycle. The hatched areas may be conceptualized as the respiratory work or effort savings that are attributed to PPAP. This work savings, as would be expected, translates to greater comfort for the PPAP assisted patient and increased compliance with the respiratory treatment. According to the present invention, PPAP therapy thus represents a novel respiratory disorder treatment by which patient comfort (and, therefore, treatment compliance) exceed that offered by either CPAP or bi-level PAP therapy.

Referring again to FIG. 1, it will thus be appreciated that pressure controller 24 is continuously governed by and outputs variable pressure responsive to a command signals 54 from PPAP circuitry 28. Command signals 54, in turn, are the product of the influences of one or more of the outputs from flow transducer 22, leak detection system 32, base pressure control 42, inspiratory gain setting control 44, expiratory gain setting control and, in an alternative embodiment, a pressure profile control 56 discussed below.

Figure 6A:
FIGS. 6A and 6B are flow and pressure diagrams, respectively, similar to FIGS. 3A and 3B, depicting alternative pressure profiles that are employed at the beginning of an inspiratory phase of respiration to facilitate the onset of inspiration.
Figure 6B:
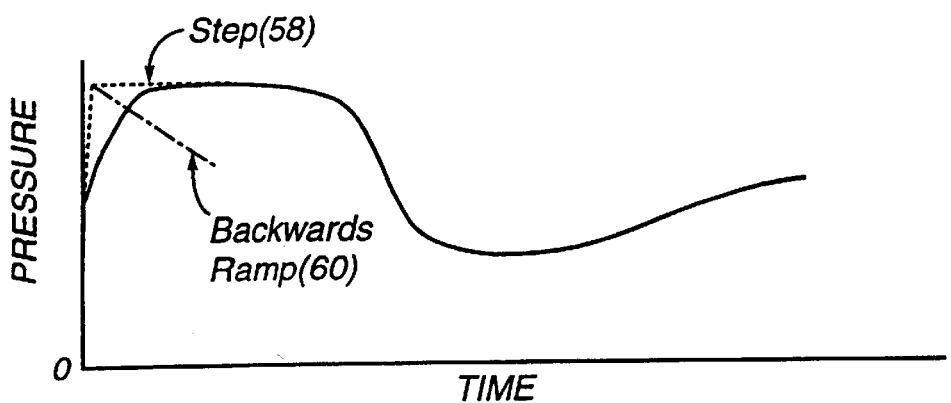

In normal breathing, a negative pressure gradient must be generated before flow can begin. Hence, the negative pressure waveform generated in the airway must precede and thereby induce inspiratory flow at the start of inspiration. In an unstable airway, which is characteristic of OSAS, for example, this asynchronous relationship of negative pressure gradient and inspiratory flow onset would, if not accommodated by suitable compensatory measures, lead to a situation where the PPAP therapy would not generate sufficient pressure (due to low flow) to overcome the negative pressure in the airway, whereby total or partial airway collapse may result. This problem can be solved by a number of methods. For instance, a higher PPAP base pressure can be used to provide additional pressure to support the airway at the beginning of inspiration. Alternatively, however, as demonstrated by FIGS. 6A and 6B, a temporary pressure increase can be added at the start of inspiration to support to the airway until sufficient flow is generated to drive the PPAP process. The present invention offers several viable approaches by means of which pressure can be added during the initial phase of inspiration to support the airway as inspiratory flow increases.

Temporary pressure increases may be effected using pressure profile control 56 in operative connection with PPAP circuitry 28 to select a desired elevated pressure waveform in the early stages of inspiration. In this regard, pressure profiles may be used as minimum values for the output pressure at the outset of inspiration, thereby giving rise to the following alternative equations for available output pressure during inspiration.

Pinhalation=greater of:

$$P\text{base}+\text{Gain}_{Insp}*\text{Flow}$$

or $$P\text{base}+P\text{profile}$$

where:

"Pinhalation" is the pressure delivered to the patient interface during inspiration "Pbase" is the base line pressure (conceptually equal to EPAP);

"Flow" is the estimated patient flow;

"$\text{Gain}_{Insp}$" is the constant used during inspiration (positive flow) to boost pressure based on the flow rate; and "Pprofile" is a function that generates a pressure profile to support the airway at the start of inspiration. Such pressure profile functions may be constant, e.g., a step profile as shown by the dotted line identified by numeral 58 in FIG. 6B, time based (for instance, a backwards ramp profile as shown by the dotted and dashed line identified by numeral 60 in FIG. 6B), or any other functional shape.

Alternatively, pressure profiles can be used exclusively to control the output pressure for a predetermined initial segment of inspiration. The following equations represent system output pressure during inspiration under such control conditions.

$$P\text{inhalation}=P\text{profile from start of breath to } X$$

and $$P\text{inhalation}=P\text{base}+\text{Gain}_{Insp}* \text{ Flow from } X \text{ to start of exhalation}$$

where:

"Pinhalation" is the pressure delivered to the patient interface during inspiration;.

"Pbase" is the base line pressure (conceptually equal to EPAP);

"Flow" is the estimated patient flow;

"$\text{Gain}_{Insp}$" is the constant used during inspiration (positive flow) to boost pressure based on the flow rate; and "Pprofile" is any function that generates a pressure profile to support the airway at the start of inspiration. Such functions could be constant, such as, for example, a step profile, or time based, such as a backwards ramp profile, or any other functional shape.

"X" is a preselected transition point determined by time, or analysis of the flow signal, such as curvature, percent drop from peak flow rate, integration, derivative, analysis of prior breaths or a combination of flow analysis and time.

The PPAP apparatus 10 also has the capacity to measure and store in a memory 62 (FIG. 1) the following parameters: tidal volume, inspiratory time, expiratory time, peak pressure, peak flow, $O_2$ saturation (as a voltage input from an external source), plural pressure (as a voltage input from an outside-source), mask pressure, estimated leakage, and system parameters, e.g., Pbase, Auto $\text{Gain}_{Insp}$, $\text{Gain}_{Insp}$, $\text{Gain}_{Esp}$, IPAP and EPAP. It is to be understood that this list is not exclusive; other parameters can be stored in memory 62.

Figure 7A:
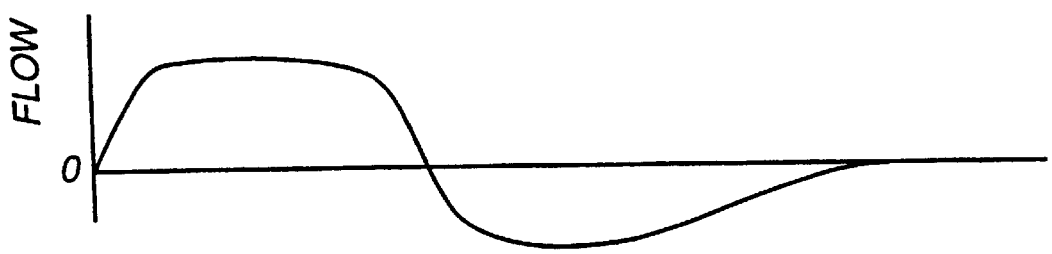
FIGS. 7A and 7B are flow and pressure diagrams, respectively, similar to FIGS. 3A and 3B, illustrating a resultant apparatus pressure output curve according to a further embodiment of the present invention.
Figure 7B:
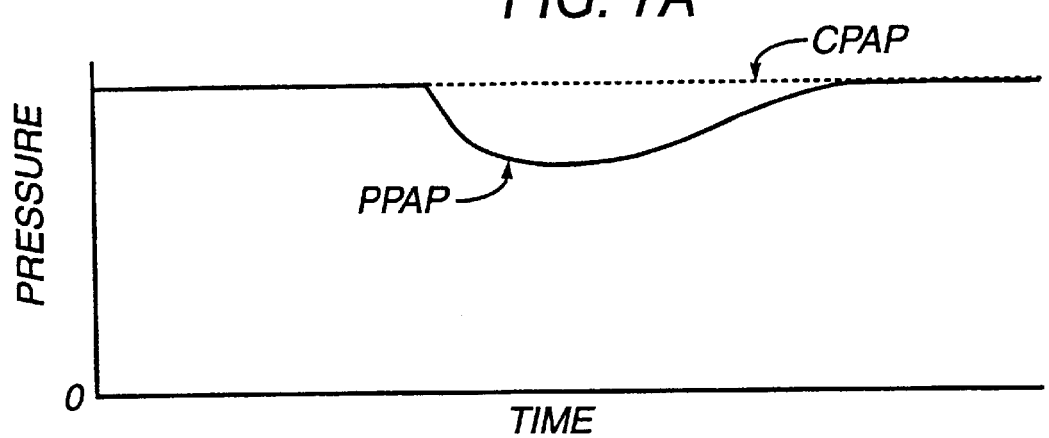

A further method by which the present system addresses the problem presented by the changing needs of the patient is to combine the beneficial features of PPAP with a more controlled therapy such as CPAP, as is shown in FIGS. 7A and 7B.

With CPAP, a single pressure is generated and delivered throughout the sleeping session. PPAP can be advantageously joined with CPAP to lower the pressure provided to the patient during exhalation. The resulting equations for pressure delivered under combined PPAP-CPAP are as follows:

$$P\text{inhalation}=\text{CPAP}$$

and $$P\text{exhalation}=\text{CPAP}+\text{Gain}_{Exp}*\text{Flow}$$

where:

"$\text{Gain}_{Exp}$" is the constant used during exhalation (negative flow) to reduce pressure based on the flow rate.

Figure 8A:
FIGS. 8A and 8B are flow and pressure diagrams, respectively, similar to FIGS. 3A and 3B, showing a resultant apparatus pressure output curve achieved by combing a conventional bi-level positive airway pressure therapy with the proportional positive airway pressure therapy according to the instant invention.
Figure 8B:
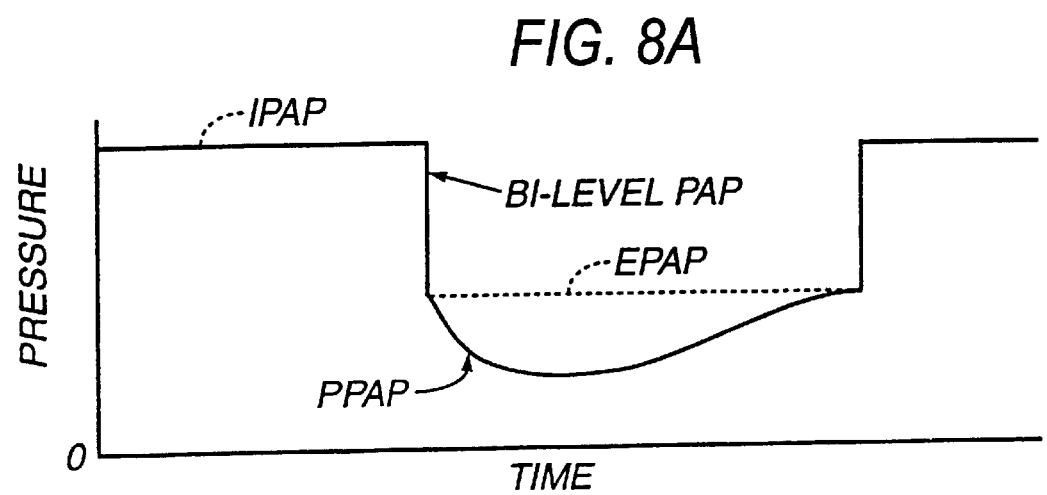

FIGS. 8A and 8B demonstrate that PPAP can also be combined with bi-level PAP therapy in a number of ways to produce effective therapeutic pressure waveforms. One application, generally similar to the aforementioned PPAP-CPAP scenario, is to use PPAP to lower the pressure during exhalation. The resulting equations for the delivery of composite PPAP—bi-level PAP pressure are as follows:

$$P\text{inhalation}=\text{IPAP}$$

and $$P\text{exhalation}=\text{EPAP}+\text{Gain}_{Exp}*\text{Flow}$$

where:

"$\text{Gain}_{Exp}$" is the constant used during exhalation (negative flow) to reduce pressure based on the flow rate.

Figure 9A:
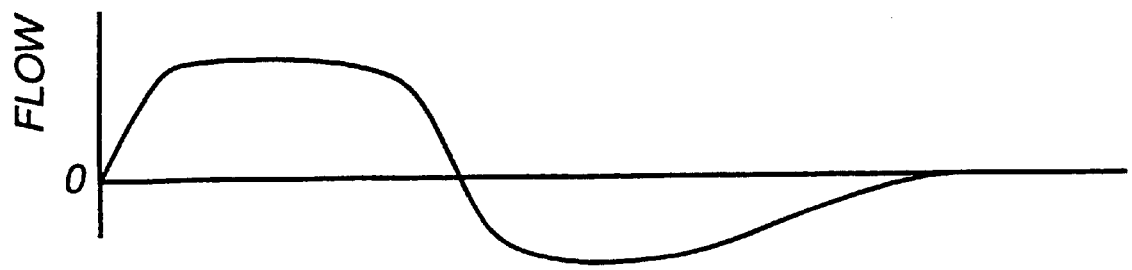
FIGS. 9A and 9B are flow and pressure diagrams, respectively, similar to FIGS. 3A and 3B, reflecting a further resultant apparatus pressure output curve achieved by combining a conventional bi-level positive airway pressure therapy with proportional positive airway pressure therapy according to the instant invention.
Figure 9B:
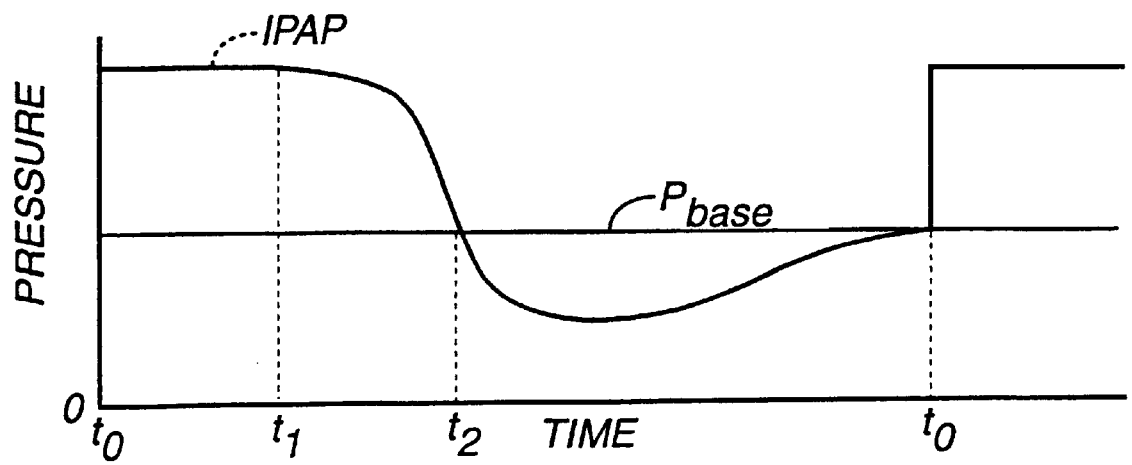

Another approach to merging PPAP with bi-level-therapy is shown in FIGS. 9A and 9B where IPAP is applied to the patient for a first portion of the inspiratory cycle and PPAP is applied for the remainder of the breathing cycle. $\text{Gain}_{Insp}$ is automatically calculated for each breath based on IPAP and the flow rate as follows:

$$P\text{inhalation } (t_0 \text{ to } t_1) = \text{IPAP}$$

and $$P\text{inhalation } (t_1 \text{ to } t_2) = P\text{base} + \text{AutoGain}_{Insp} * \text{Flow}$$

and $$P\text{exhalation} = P\text{base} + \text{Gain}_{Exp} * \text{Flow}$$

where:
"Flow" is the estimated flow rate;
"$t_0$" is the time at the start of breath;
"$t_1$" is the time when the estimated flow rate is a predetermined percentage of peak inspiratory flow rate;
"$t_2$" is the time at the start of exhalation;
"IPAP" is a continuously applied inspiratory positive airway pressure;
"Pinhalation ($t_0$ to $t_1$)" is the pressure delivered to the patent from $t_0$ to $t_1$;
"Pbase" is a continuous base pressure;
"$\text{AutoGain}_{Insp}$" equals (IPAP-Pbase)/Flow at $t_1$;
"Pinhalation ($t_1$ to $t_2$)" is the pressure delivered to the patient from $t_1$ to $t_2$;
"$\text{Gain}_{Exp}$" is the constant used during exhalation to reduce pressure delivered to the patient; and
"Pexhalation" is the pressure delivered to the patient during exhalation.

It is to be understood that the flow and PPAP pressure output curves of FIGS. 3A through 9B represent the apparatus output pressure and flow during the inspiratory and expiratory phases of a single respiratory cycle. The PPAP and flow curves can, of course, be expected to vary somewhat from respiratory cycle to respiratory cycle depending on the patient's respiratory requirements, particularly under fully automated PPAP therapy described hereinafter. Furthermore, somewhat greater variations will likely occur between the respiratory cycles associated with different stages of an extended treatment session, especially during OSAS treatment.

Figure 2:
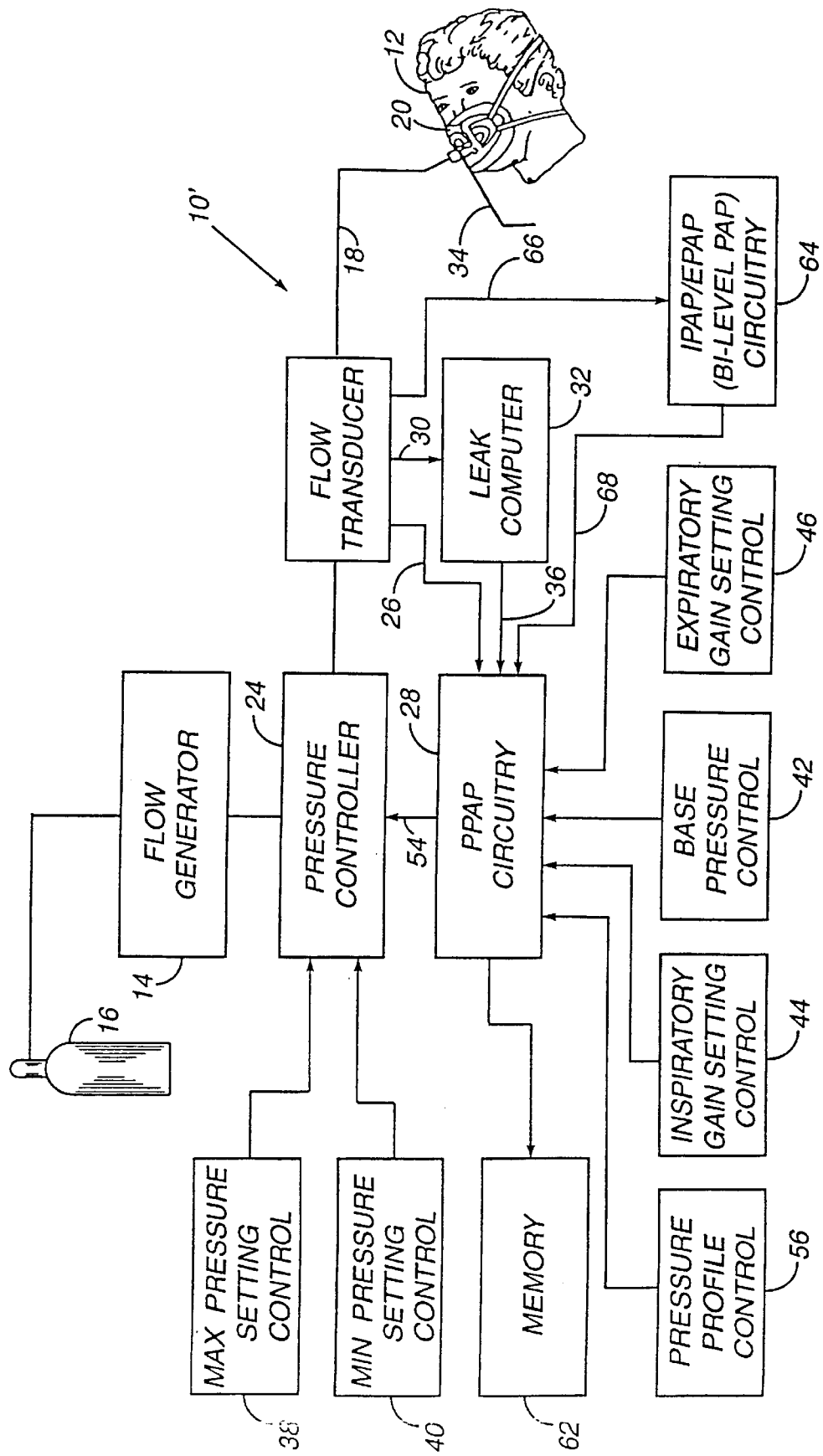
FIG. 2 is a functional block diagram of a further embodiment of an apparatus according to the instant invention.

FIG. 2 represents a further preferred embodiment of a PPAP apparatus pursuant to the present invention, designated herein by reference numeral 10'. Apart from the addition IPAP/EPAP (bi-level PPAP) circuitry 64, PPAP apparatus 10' is identical in structure and function to PPAP apparatus 10. According to this embodiment, output 66 from flow transducer 22 is fed to bi-level PAP circuitry 64. Bi-level PAP circuitry 64 may assume any conventional form such as, for example, that described in U.S. Pat. Nos. 5,148,802; 5,433,193; and 5,632,269, the contents or which are incorporated herein by reference. Output 68 from bi-level PPAP circuitry 64 is transmitted to the PPAP circuitry 28. Output 68 consists of an IPAP signal if the patient is inhaling and an EPAP signal in the event the patient is exhaling. The logic of the PPAP circuitry 28 utilizes this input according to a preselected one any of the aforementioned combinations of PPAP-bi-level therapy to generate a desired pressure command signal 54.

Pursuant to the present invention, the pressure delivered to the patient is determined by the base pressure, the flow rate and the gain (and the pressure profile if used). For a given patient condition, these settings can be adjusted as necessary to stabilize the airway. In OSAS, a patient's periodic and, to a lesser extent, instantaneous condition is variable with sleep state and body position. Thus, settings that may work well in during one portion of a sleeping session may not work as well at a different time. In other words, settings that support the airway at its most unstable state may cause pressures that are higher than necessary during more stable times. Likewise, settings that work well at one point in the session may be insufficient at another time.

The present invention proposes several methods to minimize the impact of the patient's changing needs on the optimization of PPAP therapy. One such method is to automatically adjust the gain, pressure profile and baseline pressure to meet the patient's demands. This adjustment can be based on analysis of patient parameters related to flow, e.g., magnitude, shape, derivative, integral (volume), pressure, snoring, arterial oxygen saturation, exhaled $CO_2$, airway diameter, or other parameters.

Using one or more of these parameters the system may adjust the $\text{Gain}_{Insp}$ to prevent partial airway obstruction (hypopnea). The goal of such systems is to increase $\text{Gain}_{Insp}$ responsive to any of the following patient conditions:
decreased inspiratory flow;
decreased inspiratory volume;
increased airway resistance, as determined by flow or pressure signal analysis;
airway instability, as indicated by pressure or sound variations;
drops in arterial oxygen saturation; or
decreases in airway diameter.

The apparatus according to the invention may also maintain minimal $\text{Gain}_{Insp}$ in the absence of these conditions.

The present system may also adjust the base pressure (Pbase) to prevent complete collapse of the airway (apnea) or severe collapse (severe hypopnea). Apnea can be detected by analysis of the flow signal and/or by using reflected pressure waves, or a combination of pressure and flow to determine airway patency. Moreover, it may be important to determine if the apnea is caused by airway collapse or by a lack of respiratory drive. If an obstructive event is detected the base pressure can therefore be increased to open the airway. A further capability of the present system is to maintain a minimum Pbase in the absence of these conditions.

The system may also adjust the pressure profile (Pprofile) to prevent apnea or hypopnea at the onset of inspiration. As such, the system may increase Pprofile in response to decreased inspiratory flow, decreased respiratory volume, flow waveform shape analysis that indicates increasing airway resistance, pressure or sound variations indicative of airway instability, drops in arterial oxygen saturation, decreases in airway diameter or a change in exhaled $CO_2$. Commensurate, therewith, the present invention also functions to maintain the minimum pressure profile in the absence of these conditions.

Figure 10:
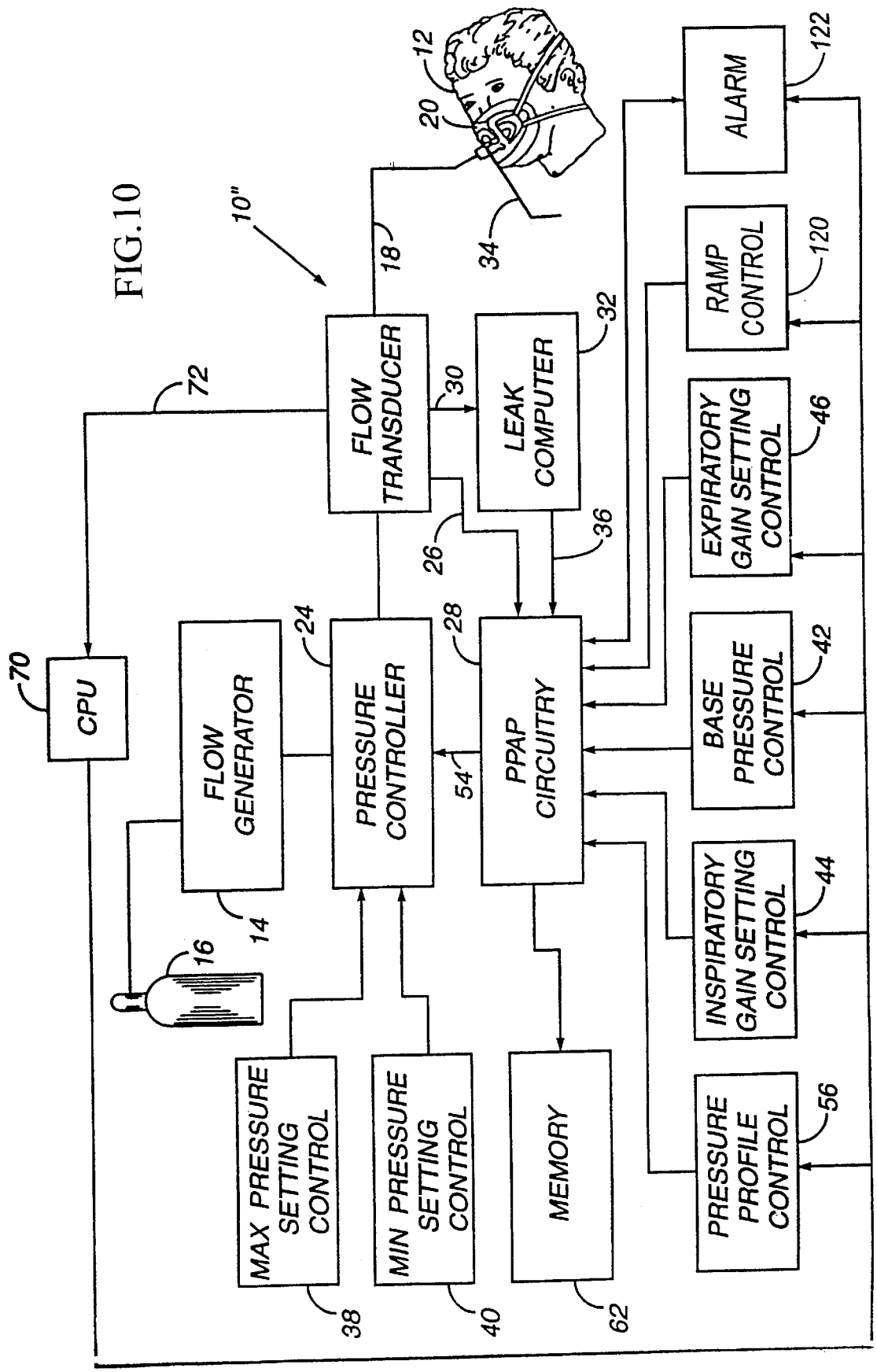
FIG. 10 is a functional block diagram of a further embodiment of an apparatus according to the instant invention

FIG. 10 reveals a presently preferred embodiment of a fully automated PPAP apparatus 10" constructed according to the present invention. Generally similar in structure and function to PPAP apparatus 10 of FIG. 1, PPAP apparatus 10" additionally incorporates a microprocesser or central processing unit (CPU) 70 that preferably utilizes an output signal 72 from flow transducer 28 as a continuous feedback signal to enable the CPU to continuously adjust Pbase, Pprofile, $\text{Gain}_{Insp}$, and $\text{Gain}_{Exp}$ as necessary. The CPU may, however, be configured to effect its continuous system control functions responsive to any of the aforementioned patient parameters related or unrelated to respiratory flow.

Apparatus 10″ also has the capability to detect hypopnea, as evidenced by decreases in peak flow and/or tidal volume for a given period of time, and the occurrence of apneas, as manifested by very little flow for a given period of time. To detect hypopnea, for example, the CPU 70 may be programmed to make a comparison between a short term average of peak inspiratory flow rate or tidal volume (e.g., a 3 breath average) and a long term average of peak flow rate or tidal volume (e.g., greater than 20 breaths). If a decrease of greater than 25% is detected the system determines a hypopnea to be present. This determination is desirably made only if the leakage is well estimated and stable. Thus, large changes in leak or initiation of a leak recovery will cause data to be ignored.

The invention further includes a method for determining if the airway is open (central apnea) or obstructed (obstructive apnea) during an apnea. Once an apnea of significant duration is detected the system, under the direction of CPU 70, automatically increases $Gain_{Insp}$ by 2 cm $H_2O$, waits approximately 1 second and decreases the pressure back to the original value. If there is a significant change in flow during this pressure change, the system concludes that the airway is open (central apnea). If there is no significant change in flow the system determines that the airway is obstructed (obstructive apnea). The system will continue to monitor each apnea for its entire duration at periodic intervals to determine the nature of the apnea.

In accordance with a preferred embodiment, the PPAP apparatus 10″ controls are automatically adjusted as follows. In the event of a hypopnea, $Gain_{Insp}$ is increased by 2 cm/liter/second. In the event of an obstructive apnea, Pbase is increased by 1 cm $H_2O$. The device will continue to increase Pbase as long as an obstructive apnea of significant duration is detected. The device will not increase $Gain_{Insp}$ again, if necessary, until 5 breaths have passed. If no hypopnea or apneas occur over a period of 30 breaths, $Gain_{Insp}$ is decreased by 1 cm/liter/second. If no hypopnea or apneas occur over a period of 50 breaths, Pbase is decreased by 1 cm $H_2O$. In addition, the apparatus may control the delivery of $O_2$ while patient flow is greater than zero, if such desired or necessary.

Although not illustrated, still further embodiments of the present invention contemplate the incorporation of fully automated PPAP with CPAP and/or bi-level PAP therapy. In these cases CPAP or IPAP may be controlled using the same logic that controls $Gain_{Insp}$ in the above-described fully automated PPAP system. Likewise, Pbase may be controlled in a similar manner to that described in connection with fully automated PPAP.

The fully automated PPAP-CPAP or PPAP-bi-level PAP systems may also adjust Pprofile to prevent apnea or hypopnea at the start of inspiration. Such systems may therefore increase CPAP (or IPAP) or Pprofile in the face any of the following patient conditions:

decreased inspiratory flow;

decreased inspiratory volume;

increased airway resistance, as determined by flow or pressure signal analysis;

airway instability, as indicated by pressure or sound variations;

drops in arterial oxygen saturation; and decreases in airway diameter.

It will be understood that CPAP or IPAP would be maintained at minimal levels in the absence of these conditions.

Using PPAP therapy, therefore, it is additionally possible to employ PPAP in response to expiratory flow to reduce pressure applied during expiration to less than the patient's PEEP level throughout all but the end of the expiratory phase in a manner similar to that described for lowering the pressure below Pbase during exhalation in the treatment of OSAS. This lowering of applied pressure to less than PEEP during the expiratory phase diminishes breathing work and enhances patient comfort when compared to the constant expiratory phase pressure applied during EPAP. Indeed, PPAP can be adapted to any ventilation mode that uses PEEP. Such applications may include pressure support with PEEP, PAV with PEEP or other applications of PEEP in respiratory assistance therapy.

Furthermore, the administration of oxygen in phase with inspiration may also easily be included with PPAP therapy for the treatment of COPD patients requiring supplemental oxygen.

The present invention also contemplates that the pressure of the gas being provided to the patient can be controlled so as to vary over time. For example, in one embodiment of the present invention, the pressure provided to the patient increases from a first minimum pressure to a desired therapy pressure over a period of time. This ramp increase in pressure provides the patient with time to fall asleep under relatively low pressure that is increased to the therapy pressure over time. Thereafter, the pressure increases so that the therapy pressure is being applied after the patient is asleep. A reverse process can be performed in the morning, with the pressure being decreased from the therapy pressure shortly before the patient intends to wake up. Ramp control 120 in FIG. 10 schematically illustrates a manually actuated controller that provides commands to PPAP circuitry 28 to cause the pressure to be provided according to a ramp cycle. Furthermore, the ramp control may be adjusted according to the output of CPU 70. Ramp control 120 can be used to set the parameters associated with the ramp function, such as the ramp period, ramp start time, ramp stop time, and ramp shape.

Examples of techniques for controlling the pressure level provided to the patient via one or more ramp functions, as well as other methods for controlling the patient pressure, are disclosed in U.S. Pat. Nos. 5,492,114; 5,551,418 and RE 35,295, the contents of each are incorporated herein by reference. Many of the techniques taught by these patents can be incorporated into the present apparatus and method to provide the optimum therapy necessary to treat the patient.

In a still further embodiment of the present invention, an alarm 122 is coupled to PPAP circuitry 28 and/or CPU 70. Alarm 122 can be controlled so as to be actuated as a result of a variety of circumstances. However, in a preferred embodiment of the invention, alarm 122 is actuated responsive to an automatically determined gain falling outside a predetermined range of values.

The present invention also contemplates limiting a value for an automatically determined gain, such as $AutoGain_{Insp}$ discussed above, to prevent the automatically determined gain from exceeding predetermined limits, for example, from exceeding limits that may result in an excessively high pressure being provided to the patient The limits on the amount that the gain can themselves be altered sol that these limits vary over a predetermined period of time. Also, the amount of change that may take place in the automatically determined gain over a predetermined period of time can also be controlled, thereby preventing the automatically determined gain from changing by more than a predetermined amount over the predetermined period of time.

In using PPAP to treat CHF, the present invention reduces mean pressure and work of exhalation while still providing the same level of rest to the heart. By applying a positive base pressure substantially equivalent to a pressure needed to reduce cardiac preload and afterload (preferably in the range of 5–10 cm $H_2O$), the present invention helps the heart reduce its efforts. With additional positive pressure: during inspiration in proportion to respiratory effort, one can overcome the effect of negative pressure being produced during inspiration. PPAP is particularly appropriate in CHF patients in that the typical CHF patient has normal lung compliance. In these patients, much of the respiratory loading can be inferred from the flow signal. By reducing the pressure below the base pressure during exhalation, one can reduce the work of exhalation without, reducing the benefit to the heart. The net effect will be the same benefit to the heart with reduced work of breathing and lower mean pressure.

Similar to PPAP therapy's use for preventing airway collapse, PPAP therapy for the treatment of CHF delivers only the minimum amount of pressure needed to reduce cardiac preload and afterload. This will result in supplying a base pressure to the exterior of the heart equivalent to the pressure needed to reduce cardiac preload and afterload in the absence of respiratory loading and a varying pressure which is needed to overcome the impact of respiratory loading on cardiac preload and afterload while minimizing the work of breathing.

Supplying positive pressure to the exterior of the heart via the respiratory system has two benefits firstly, the positive pressure will reduce the enlarged heart of a CHF patient to a size closer to normal. This return to normal size, allows the muscles of the heart to work more effectively. Secondarily, the positive pressure in the chest cavity reduces the amount of pressure the heart must overcome to pump blood to the rest of the body.

The heart and chest cavity are at the same pressure. Typically this pressure fluctuates about ambient pressure due to the impact of respiratory loading. The circulatory system has a working pressure that varies as the heart pumps but averages 100 mm HG in normal-tensive patients. The heart must supply the power to force blood from the chest cavity into the pressurized circulatory system. Increasing the pressure in the chest cavity reduces the amount of pressure the heart must over come to pump blood. A pressure in the chest cavity of 10 cm $H_2O$ or approximately 10 mm Hg will reduce the load on the heart by 10 mm Hg/100 mm Hg or roughly 10%.

The impact of respiratory effort on the heart is as follows: during inspiration, the pressure in the chest (and thus surrounding the heart) becomes more negative relative to the rest of the body. This increased negative pressure increases the amount of pressure the heart must generate to pump blood from the chest cavity to the body. By providing pressure in excess of the base pressure during inspiration, PPAP is able to offset this decrease in chest cavity pressure and maintain a relatively constant pressure in the chest.

During exhalation the pressure in the chest becomes less negative relative to the rest of the body. By reducing the pressure during exhalation, PPAP is able to offset the increase in chest cavity pressure and maintain a relatively constant pressure in the chest.

By minimizing the decrease in pressure and taking advantage of the increased pressure during exhalation, the variable portion of PPAP allows a lower baseline to be set relative to using a constant pressure with the same benefits to the heart. This lower baseline and reduced pressure during exhalation also reduces the work of breathing and increases patient comfort.

It is further desirable to implement a version of PPAP similar to that discussed above with respect to FIG. 7 on existing CPAP devices. Providing a version of PPAP on existing CPAP devices enhances the patient comfort and, hence, compliance without the significant financial and other burdens appurtenant to manufacturing and introducing a new CPAP device that includes a PPAP mode. Providing a PPAP therapy on a CPAP device can be accomplished in a variety of ways, such as that discussed above with respect to FIGS. 7A and 7B.

A version of PPAP can be implemented on a CPAP system in a more cost effective manner if the reactive component used to generate the reduced pressure curve during exhalation in FIG. 7 is replaced with a defined reduced pressure profile. This pressure profile replaces the constant CPAP pressure otherwise applied by the CPAP device during the expiratory phase of the patient's breathing cycle. In an preferred embodiment of the present invention, the defined pressure profile has a shape that generally corresponds to a patient's normal flow.

Figure 11A:
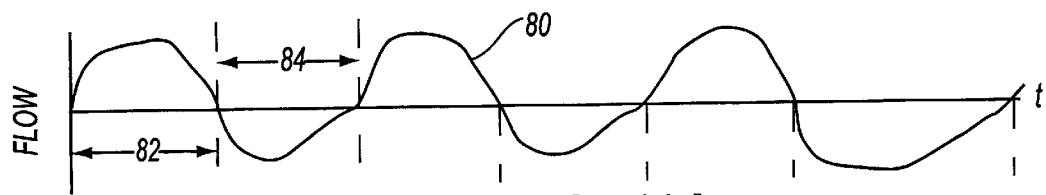
FIGS. 11A and 11B are flow and pressure diagrams, respectively, similar to FIGS. 7A and 7B, illustrating a resultant apparatus pressure output curve according to a further embodiment of the present invention that utilizes a simplified pressure profile generating technique.
Figure 11B:
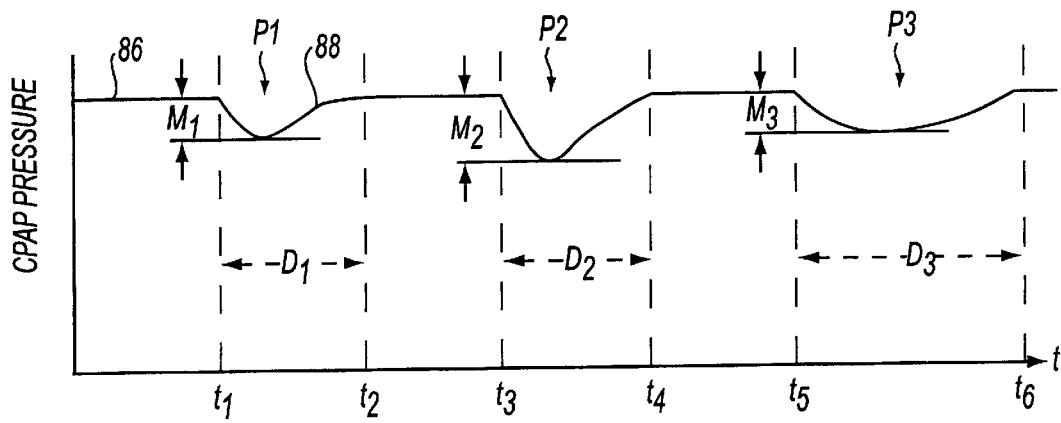

FIGS. 11A and 11B are flow and pressure diagrams similar to FIGS. 7A and 7B illustrating a resultant apparatus pressure output curve according to a further embodiment of the present invention that utilizes a simplified pressure profile generating technique. Flow signal 80 in FIG. 11A illustrates the patient's inspiratory phase 82 and expiratory phase 84. As shown in FIG. 11B, a continuous CPAP pressure 86 is delivered during the inspiratory phase 82. During the expiratory phase, the pressure support device is controlled to deliver a reduced pressure following a predetermined pressure profile 88. The resulting equations for pressure delivered under the combined CPAP and PPAP are as follows:

$P$inhalation=CPAP and $P$exhalation=CPAP—Predetermined Pressure profile.

The predetermined pressure profile, which is used to reduce the CPAP pressure, has a magnitude M, which is typically selected by a respiratory therapist in a range of 0–4 $cmH_2O$, and a duration D that, unlike the pressure curve in FIG. 7B, is not directly determined base on the patient's instantaneous flow or volume. The magnitude M represents the drop in pressure from the constant CPAP value. The duration, D value is preferably a fraction of an average expiration period of the patient.

Multiple predefined pressure profiles, having different magnitudes, durations or both can be stored in a CPAP/PPAP device and provided to the patient. FIG. 11B illustrates three predetermined pressure profiles P1, P2 and P3, having magnitudes M1, M2 and M3 and durations D1, D2 and D3, respectively. In a preferred embodiment of the present invention, the pressure profiles are selected so that the pressure provided to the patient during exhalation roughly correspond to the contour generated from flow or volume based PPAP, as shown, for example, in FIGS. 3A and, 3B. As shown in FIG. 11B, the pressure drops off quickly at the start of expiration then rises slowly toward the baseline CPAP pressure.

Because this embodiment for a CPAP/PPAP device does not control the flow and/or pressure provided to the patient based on the flow or pressure signal from the patient, as is the case with the PPAP devices and techniques discussed above, but instead, merely detects the start or expiration and/or inspiration, the sensor required by this embodiment need not be as accurate as in the previous embodiments. For example, a thermister or thermocouple could replace the costly pneumotach flow meter to determine the inspiratory and expiratory state. Also, the pressure profile provided to the patient during the expiratory phase can be generated using motor speed control, thereby avoiding the use of a pressure control valve.

While the above embodiment has been described above with respect to the use of a predetermined pressure profiled used to reduce a CPAP pressure during expiration, the same technique can be applied to a bi-level pressure supported device to achieve a pressure curve shown, for example, in FIG. 8B by reducing the bi-level EPAP pressure by the predetermined pressure profile.

Figure 12:
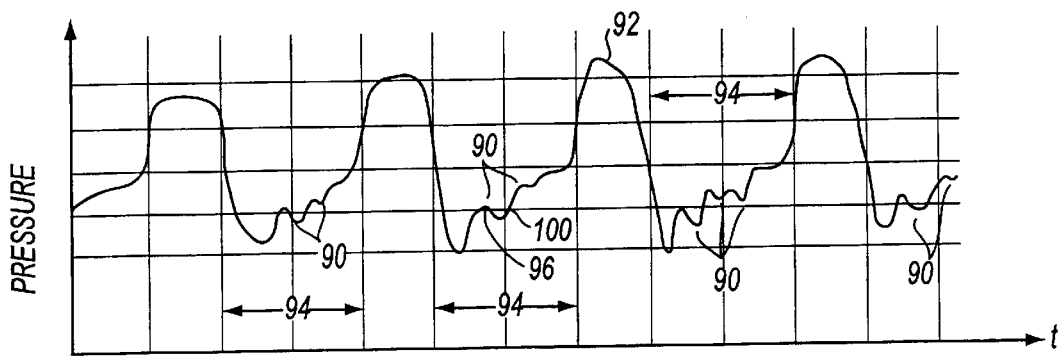
FIG. 12 is a pressure diagram illustrating the occurrence of oscillations in the pressure provided to the patient during exhalation.

It has been observed that in some cases where PPAP is implemented and the gain is set above a certain amount, for example beyond the range of 2–3 cm/liter/sec, there is a tendency for the pressure generated by the device to become unstable. More specifically, as shown in FIG. 12, oscillations 90 occur in the pressure waveform 92 applied to the patient during portions of the patient's expiratory phase 94. These oscillations typically occur after the initial pressure drop following the onset of the expiratory phase and are believed to be generated as a result of the interaction of the patient's flow and the resulting pressure decrease.

Despite the chance of such oscillations occurring, it is still preferable to provide a relatively large decrease in the pressure being provided to the patient at the onset of expiration while maintaining the pressure profile as smooth as possible during the remainder of the expiratory phase. This is accomplished according to one embodiment of the present invention by providing pressure to the patient during expiration according to the following equations:

Pexhalation=the greater of:

$P$base-+Gain$_{Exp}$*Flow or

A Current Pressure, where the "Current Pressure" is the pressure being provided to the patient at that time during the expiratory phase.

Figure 13:
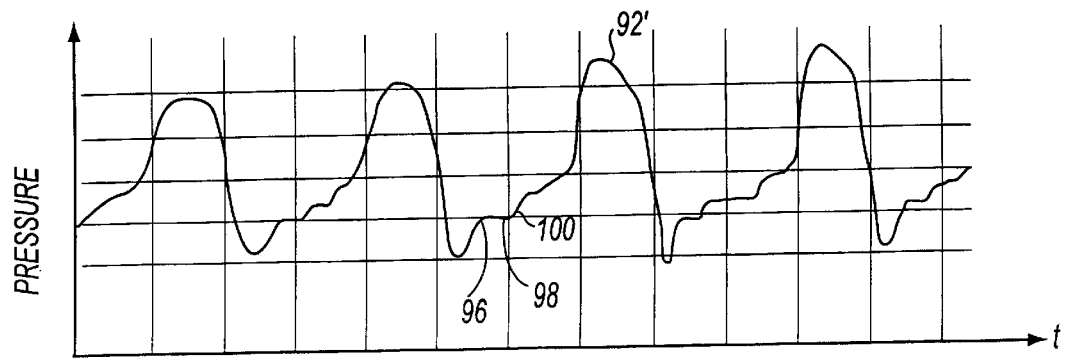
FIG. 13 is a pressure diagram illustrating a first technique for reducing the oscillations illustrated in FIG. 12.

FIG. 13 illustrates a pressure profile 92' similar to profile 92 illustrated in FIG. 12, except that the oscillations occurring during the expiratory phase have been removed using the above described technique. For example, at point 96 where the pressure begins to decrease from the immediately previous pressure due to a pressure oscillation, the above technique prevents this decrease by substituting the current pressure, i.e., the pressure at point 96 at all points thereafter where the calculated pressure, i.e., $P$base-+Gain$_{Exp}$*Flow, is less than the current pressure, thereby creating a plateau section 98 that corresponds to the pressure at point 96, i.e., the current pressure, until a point 100 where the calculated pressure becomes greater than the current pressure. It should be noted that for purposes of this invention, Flow is considered to be negative during the expiratory phase.

By ensuring that the pressure provided to the patient is always the greater of the current pressure and the calculated pressure, the pressure received by the patient during expiration does not oscillate. If the pressure to be provided to the patient begins to decrease below the current pressure, the device will not use the calculated pressure, but will continue to provide the patient with the current pressure, thereby preventing a pressure decrease below the current pressure.

In a second embodiment of the present invention, the pressure oscillations are avoided by using an entirely different calculation for determining the pressure to be provided to the patient during the expiratory phase. Instead of basing the calculation of the pressure to be provided to the patient based on the patient flow multiplied by a gain, which is selected either manually or automatically, as in the previous embodiments, the calculation of the pressure to be provided to the patient is based on the volume of gas still contained in the lungs, referred to as the volume to be exhaled. The volume to be exhaled corresponds to a difference between a current volume of gas in the patient and a volume of gas in the patient at rest. The volume of gas currently in the lungs can be readily estimated from the flow signal. The volume of gas in the patient at rest is determined using conventional techniques, and can be updated on a periodic base to ensure the accuracy of the calculation.

According to this embodiment, the pressure output by the PPAP device at least during a portion of the expiratory phase is described by the following function, which can be encoded into the PPAP circuitry:

$P$exhalation=$P$base-(Volume$_{to\ be\ exhaled}$*Gain$_{Exp}$)

where:

"$P$base" is the base line pressure (greater than or equal to zero and conceptually equal to EPAP);

"Volume$_{to\ be\ exhaled}$" is the difference between the current volume of gas in the patient less the volume of gas in the patient at rest; and "Gain$_{Exp}$" is the constant used during expiration (negative flow) to reduce pressure.

Figure 14:
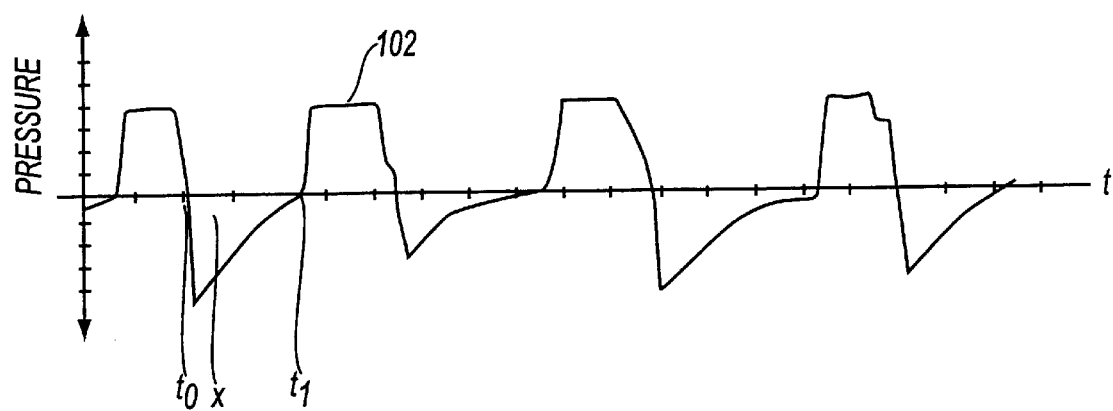
FIG. 14 is a pressure diagram illustrating a second technique for reducing the oscillations illustrated in FIG. 12.

The pressure output during the inspiratory phase is determined using the techniques discussed above. FIG. 14 illustrates a pressure curve 102 generated using the above equation to determine the pressure to be provided to the patient. It can be appreciated from FIG. 14 that pressure curve 102 accomplishes the functions of lowering the pressure during expiration and returning the pressure to the baseline at the end of the expiratory phase, preventing airway collapse.

Because the volume of gas to be exhaled (Volume$_{to\ be\ exhaled}$) is relatively large at the onset of the expiratory phase, the pressure drop at the beginning of exhalation can be quite large. It is preferable to smooth the large drop at the onset of the expiratory phase by including a dampening factor in the calculation of the pressure to be provided to the patient.

There are many techniques that can be used to dampen the initial pressure drop at the start of the expiratory phase. However, according to a preferred embodiment of the present invention, the pressure provided to the patient during the expiratory phase is described according to the following equation:

from the start of the expiratory phase ($t_0$) to X:

$$P\text{exhalation} = P\text{base} - \frac{t}{X}(\text{Volume}_{\text{to be exhaled}} * \text{Gain}_{\text{Exp}})$$

and from X to the end of the expiratory phase ($t_1$):

$P$exhalation=$P$base-(Volume$_{to\ be\ exhaled}$*Gain$_{Exp}$)

where:

"t" is a current time following the start of the expiratory phase; and

"X" is a predetermined transition point after the start of the expiratory phase determined by time, or analysis of the flow signal, such as curvature, percent drop from peak flow rate, integration, derivative, analysis of prior breaths or a combination of flow analysis and time.

As shown in FIG. 14, the value of X is chosen so that the pressure provided to the patient during the initial period from $t_0$ to X is calculated taking into consideration the dampening factor t/X, thereby reducing the pressure drop at the onset of exhalation. Thereafter, the dampening factor is not taken into consideration and the exhalation pressure to be applied to the patient is calculated according to the second of the above two equations. Thus, this embodiment of the present invention provides a smooth pressure curve throughout the expiratory phase while ensuring that the initial pressure drop at the start of the exhalation is within expectable parameters.

It is to be understood that any other dampening technique for smoothing the size of the initial pressure drop at the start of the expiratory phase can be used in this embodiment. Thus, the present invention is not limited to the dampening technique discussed above.

Although the invention has been described in detail for the purpose of illustration based on what is currently considered to be the most practical and preferred embodiments, it is to be understood that such detail is solely for that purpose and that the invention is not limited to the disclosed embodiments, but on the contrary, is intended to cover modifications and equivalent arrangements that are within the spirit and scope of the appended claims.

What is claimed is:

1. An apparatus for delivering pressurized breathing gas to an airway of a patient, comprising:
   a gas flow generator;
   a patient interface coupled to the gas flow generator to communicate a flow of breathing gas from the gas flow generator with an airway of a patient;
   a sensor associated with the gas flow generator or the patient interface that detects a fluid characteristic associated with the flow of breathing gas within the patient interface and outputs a signal corresponding to the fluid characteristic;
   a pressure controller associated with the gas flow generator or the patient interface to control a pressure of the flow of breathing gas delivered to a patient;
   an input device; and
   processing means, adapted to receive the signal output from the sensor, and an inspiratory gain and an expiratory gain from the input device, for producing a command signal, which is determined as:
   (1) a product of the inspiratory gain and the fluid characteristic during at least a portion of an inspiratory phase of such a patient's breathing cycle, and
   (2) a product of the expiratory gain and the fluid characteristic during at least a portion of an expiratory phase of such a patient's breathing cycle, and
   wherein the processing means provides the command signal to the pressure controller so that a pressure of the breathing gas delivered to a patient varies during at least a portion of the inspiratory phase and during at least a portion of the expiratory phase with fluctuations of the fluid characteristic.

2. The apparatus of claim 1, wherein the patient interface includes a conduit, and wherein the pressure controller is a valve associated with the conduit that exhausts gas from the conduit to control the pressure of the flow of breathing gas delivered to the patient.

3. The apparatus of claim 1, wherein the sensor substantially continuously detects the fluid characteristic and substantially continuously outputs the signal to the processing means.

4. The apparatus of claim 1, wherein the processing means determines the command signal and provides it to the pressure controller substantially continuously.

5. The apparatus of claim 1, wherein the processing means determines the command signal according to:
   (1) a pressure profile from a start of the inspiratory phase to a transition point occurring during the inspiratory phase, and
   (2) based on the product of the inspiratory gain and the fluid characteristic from the transition point to the end of the inspiratory phase, so that a pressure of the flow of breathing gas delivered to the patient varies with fluctuations of the fluid characteristic.

6. The apparatus of claim 5, wherein the pressure profile corresponds to a time-based transition from a pressure at a start of the inspiratory phase to an inspiratory positive airway pressure (IPAP).

7. The apparatus of claim 5, wherein the signal from the sensor is indicative of the flow of breathing gas, and wherein the transition point is determined by the processing means based the flow of breathing gas.

8. The apparatus of claim 1, wherein the processing means determines the command signal according to:
   (1) an inspiratory positive airway pressure (IPAP) from a start of the inspiratory phase to a transition point occurring during the inspiratory phase, and
   (2) based on the product of the inspiratory gain and the fluid characteristic from the transition point to the end of the inspiratory phase, so that a pressure of the flow of breathing gas delivered to the patient varies with fluctuations of the fluid characteristic.

9. A method of delivering pressurized breathing gas to an airway of a patient, comprising:
   generating a flow of breathing gas;
   sensing a fluid characteristic associated with the flow of breathing gas and outputting a signal corresponding to the fluid characteristic;
   selecting an inspiratory gain and an expiratory gain; and
   controlling a pressure of the flow of breathing gas delivered to a patient based on:
   (1) a product of the inspiratory gain and the fluid characteristic during at least a portion of an inspiratory phase of such a patient's breathing cycle, so that a pressure of the flow of breathing gas delivered to the patient varies with fluctuations of the fluid characteristic, and
   (2) a product of the expiratory gain and the fluid characteristic during at least a portion of an expiratory phase of such a patient's breathing cycle, so that a pressure of the flow of breathing gas delivered to the patient varies with fluctuations of the fluid characteristic.

10. The method claim 9, wherein generating the flow of breathing gas includes carrying the flow of breathing gas to an airway of a patient via conduit, and wherein controlling the pressure of the flow of breathing gas includes exhausting gas from the conduit.

11. The method of claim 9, wherein sensing the fluid characteristic includes substantially continuously monitoring the fluid characteristic substantially continuously outputting the signal indicative of the fluid characteristic.

12. The method of claim 9, wherein controlling a pressure of the flow of breathing gas is done substantially continuously during a breathing cycle based on the output from the sensor, the inspiratory gain, and the expiratory gain.

13. The method of claim 9, wherein controlling a pressure of the flow of breathing gas delivered to a patient includes controlling the pressure of the flow of breathing gas according to:

(1) a pressure profile from a start of the inspiratory phase to a transition point occurring during the inspiratory phase, and (2) based on a product of the inspiratory gain and the fluid characteristic from the transition point to the end of the inspiratory phase, so that a pressure of the flow of breathing gas delivered to the patient varies with fluctuations of the fluid characteristic.

14. The method of claim 13, wherein the pressure profile corresponds to a time-based transition from a pressure at a start of the inspiratory phase to an inspiratory positive airway pressure (EPAP).

15. The method of claim 13, wherein the signal from the sensor is indicative of the flow of breathing gas, and wherein the transition point is determined based the flow of breathing gas.

16. The method of claim 9, wherein controlling a pressure of the flow of breathing gas delivered to a patient based includes controlling the pressure of the flow of breathing gas based on:

(1) an inspiratory positive airway pressure (IPAP) from a start of the inspiratory phase to a transition point occurring during the inspiratory phase, and (2) based on a product of the inspiratory gain and the fluid characteristic from the transition point to the end of the inspiratory phase, so that a pressure of the flow of breathing gas delivered to the patient varies with fluctuations of the fluid characteristic.

17. A system for delivering pressurized breathing gas to an airway of a patient, comprising:

gas flow generating means for generating a flow of breathing gas;

sensing means for sensing a fluid characteristic associated with the flow of breathing gas and outputting a signal corresponding to the fluid characteristic;

gain selecting means for selecting an inspiratory gain and an expiratory gain; and pressure regulating means for controlling a pressure of the flow of breathing gas delivered to a patient based on:

(1) a product of the inspiratory gain and the fluid characteristic during at least a portion of an inspiratory phase of such a patient's breathing cycle, so that a pressure of the flow of breathing gas delivered to the patient varies with fluctuations of the fluid characteristic, and (2) a product of the expiratory gain and the fluid characteristic during at least a portion of an expiratory phase of such a patient's breathing cycle, so that a pressure of the flow of breathing gas delivered to the patient varies with fluctuations of the fluid characteristic.

18. The system of claim 17, wherein sensing means substantially continuously detects the fluid characteristic and substantially continuously outputs the signal indicative of the fluid characteristic.

19. The system of claim 17, wherein controlling a pressure of the flow of breathing gas is done substantially continuously during a breathing cycle based on the output from the sensor, the inspiratory gain, and the expiratory gain.

20. The system of claim 17, wherein the pressure regulating means controls the pressure of the flow of breathing gas according to:

(1) a pressure profile from a start of the inspiratory phase to a transition point occurring during the inspiratory phase, and (2) based on a product of the inspiratory gain and the fluid characteristic from the transition point to the end of the inspiratory phase, so that a pressure of the flow of breathing gas delivered to the patient varies with fluctuations of the fluid characteristic.

21. The system of claim 20, wherein the pressure profile corresponds to a time-based transition from a pressure at a start of the inspiratory phase to an inspiratory positive airway pressure (IPAP).

22. The system of claim 20, wherein the signal from the sensor is indicative of the flow of breathing gas, and wherein the processing means determines the transition point based the flow of breathing gas.

23. The system of claim 17, wherein the pressure controlling means controls the flow of breathing gas based on:

(1) an inspiratory positive airway pressure (IPAP) from a start of the inspiratory phase to a transition point occurring during the inspiratory phase, and (2) based on a product of the inspiratory gain and the fluid characteristic from the transition point to the end of the inspiratory phase, so that a pressure of the flow of breathing gas delivered to the patient varies with fluctuations of the fluid characteristic.

24. An apparatus for delivering pressurized breathing gas to an airway of a patient, comprising:

a gas flow generator;

a patient interface coupled to the gas flow generator to communicate a flow of breathing gas from the gas flow generator with an airway of a patient;

a sensor associated with the gas flow generator or the patient interface that detects a fluid characteristic associated with the flow of breathing gas within the patient interface and outputs a signal corresponding to the fluid characteristic;

a pressure controller associated with the gas flow generator or the patient interface to control a pressure of the flow of breathing gas delivered to a patient;

an input device; and processing means, adapted to receive the signal output from the sensor and an expiratory gain from the input device, for producing a command signal as a product of the expiratory gain and the fluid characteristic during at least a portion of an expiratory phase of such a patient's breathing cycle, and wherein the processing means provides the command signal to the pressure controller so that a pressure of the breathing gas delivered to a patient varies during at least a portion of the expiratory phase with fluctuations of the fluid characteristic.

25. The apparatus of claim 24, wherein the patient interface includes a conduit, and wherein the pressure controller is a valve associated with the conduit that exhausts gas from the conduit to control the pressure of the flow of breathing gas delivered to the patient.

26. The apparatus of claim 24, wherein the processing means determines the command signal and provides it to the pressure controller substantially continuously.

27. The apparatus of claim 24, wherein the processing means determines the command signal according to:

(1) an inspiratory positive airway pressure (IPAP) during an inspiratory phase of such a patent's breathing cycle, and (2) based on the product of the expiratory gain and the fluid characteristic during at least a portion of an expiratory phase of such a patient's breathing cycle, so that a pressure of the flow of breathing gas delivered to such a patient during at least a portion of the expiratory phase varies with fluctuations of the fluid characteristic.

28. The apparatus of claim 27, wherein the inspiratory positive airway pressure (IPAP) is set by the processing means based on an input IPAP entered via the input device.

29. A method of delivering pressurized breathing gas to an airway of a patient, comprising:

generating a flow of breathing gas;

sensing a fluid characteristic associated with the flow of breathing gas and outputting a signal corresponding to the fluid characteristic;

selecting an expiratory gain; and controlling a pressure of the flow of breathing gas delivered to a patient based on a product of the expiratory gain and the fluid characteristic during at least a portion of an expiratory phase of such a patient's breathing cycle, so that a pressure of the flow of breathing gas delivered to the patient during at least a portion of the expiratory phase varies with fluctuations of the fluid characteristic.

30. The method claim 29, wherein generating the flow of breathing gas includes carrying the flow of breathing gas to an airway of a patient via conduit, and wherein controlling the pressure of the flow of breathing gas includes exhausting gas from the conduit.

31. The method of claim 29, wherein controlling a pressure of the flow of breathing gas is done substantially continuously during at least a portion of the expiratory phase of a breathing cycle based on the output from the sensor and the expiratory gain.

32. The method of claim 29, wherein controlling a pressure of the flow of breathing gas delivered to a patient based includes controlling the pressure of the flow of breathing gas based on:

(1) an inspiratory positive airway pressure (IPAP) during an inspiratory phase of such a patent's breathing cycle, and (2) based on the product of the expiratory gain and the fluid characteristic during at least a portion of an expiratory phase of such a patient's breathing cycle, so that a pressure of the flow of breathing gas delivered to such a patient during at least a portion of the expiratory phase varies with fluctuations of the fluid characteristic.

* * * * *